US010905513B2

(12) United States Patent
Scheib et al.

(10) Patent No.: US 10,905,513 B2
(45) Date of Patent: Feb. 2, 2021

(54) SENSORS FOR DETECTING STERILE ADAPTER AND TOOL ATTACHMENT FOR USE IN A ROBOTIC SURGICAL SYSTEM

(71) Applicant: Verb Surgical Inc., Mountain View, CA (US)

(72) Inventors: Charles J. Scheib, Loveland, OH (US); Matthew Colin Vargas, San Francisco, CA (US); Andrea Bajo, Palo Alto, CA (US); Jaime Hernandez, San Jose, CA (US); Koray Sahin, Mountain View, CA (US)

(73) Assignee: Verb Surgical Inc., Santa Clara, CA (US)

( * ) Notice: Subject to any disclaimer, the term of this patent is extended or adjusted under 35 U.S.C. 154(b) by 123 days.

(21) Appl. No.: 15/847,562

(22) Filed: Dec. 19, 2017

(65) Prior Publication Data

US 2018/0168762 A1    Jun. 21, 2018

Related U.S. Application Data

(60) Provisional application No. 62/436,957, filed on Dec. 20, 2016, provisional application No. 62/436,965, (Continued)

(51) Int. Cl.
*A61B 34/30* (2016.01)
*A61B 34/00* (2016.01)
(Continued)

(52) U.S. Cl.
CPC ........ *A61B 46/10* (2016.02); *A61B 17/00234* (2013.01); *A61B 34/30* (2016.02);
(Continued)

(58) Field of Classification Search
CPC .... A61B 17/00234; A61B 2017/00115; A61B 2017/00199; A61B 2017/00203;
(Continued)

(56) References Cited

U.S. PATENT DOCUMENTS

| 4,564,270 A | 1/1986 | Willie |
| 5,255,422 A | 10/1993 | Russo |

(Continued)

FOREIGN PATENT DOCUMENTS

| CN | 106164726 A | 11/2016 |
| JP | 60-036043 | 2/1985 |

(Continued)

OTHER PUBLICATIONS

PCT Search Report and Written Opinion dated Mar. 6, 2018, for related PCT Appln. No. PCT/US2017/067706 18 Pages.
(Continued)

*Primary Examiner* — Jonathan T Kuo
(74) *Attorney, Agent, or Firm* — Womble Bond Dickinson (US) LLP

(57) ABSTRACT

Generally, a system for use in a robotic surgical system may be used to determine an attachment state between a tool driver, sterile adapter, and surgical tool of the system. The system may include sensors used to generate attachment data corresponding to the attachment state. The attachment state may be used to control operation of the tool driver and surgical tool. In some variations, one or more of the attachment states may be visually output to an operator using one or more of the tool driver, sterile adapter, and surgical tool. In some variations, the tool driver and surgical tool may include electronic communication devices configured to be in close proximity when the surgical tool is attached to the sterile adapter and tool driver.

15 Claims, 14 Drawing Sheets

Related U.S. Application Data filed on Dec. 20, 2016, provisional application No. 62/436,974, filed on Dec. 20, 2016, provisional application No. 62/436,981, filed on Dec. 20, 2016.

(51) Int. Cl.

| | | |
|---|---|---|
| *A61B 90/40* | (2016.01) | |
| *A61B 17/00* | (2006.01) | |
| *A61B 46/10* | (2016.01) | |
| *A61B 90/00* | (2016.01) | |
| *B25J 15/04* | (2006.01) | |
| *A61B 34/35* | (2016.01) | |
| *A61B 46/00* | (2016.01) | |
| *B29C 45/00* | (2006.01) | |
| *B29C 65/02* | (2006.01) | |
| *G01V 8/16* | (2006.01) | |
| *B29L 31/00* | (2006.01) | |

(52) U.S. Cl.
CPC .............. *A61B 34/35* (2016.02); *A61B 34/70* (2016.02); *A61B 46/40* (2016.02); *A61B 90/06* (2016.02); *A61B 90/40* (2016.02); *B25J 15/0466* (2013.01); *B29C 45/0053* (2013.01); *B29C 65/02* (2013.01); *A61B 34/25* (2016.02); *A61B 34/74* (2016.02); *A61B 34/76* (2016.02); *A61B 90/361* (2016.02); *A61B 2017/00115* (2013.01); *A61B 2017/00199* (2013.01); *A61B 2017/00203* (2013.01); *A61B 2017/00207* (2013.01); *A61B 2017/00216* (2013.01); *A61B 2017/00221* (2013.01); *A61B 2017/00477* (2013.01); *A61B 2017/00486* (2013.01); *A61B 2017/00876* (2013.01); *A61B 2034/302* (2016.02); *A61B 2034/742* (2016.02); *A61B 2034/743* (2016.02); *A61B 2034/744* (2016.02); *A61B 2090/0811* (2016.02); *A61B 2090/0812* (2016.02); *A61B 2090/0813* (2016.02); *B29L 2031/7546* (2013.01); *G01V 8/16* (2013.01); *Y10S 901/41* (2013.01); *Y10S 901/46* (2013.01); *Y10S 901/47* (2013.01); *Y10S 901/49* (2013.01)

(58) Field of Classification Search
CPC ........... A61B 2017/00207; A61B 2017/00216; A61B 2017/00221; A61B 2017/00477; A61B 2017/00486; A61B 2034/302; A61B 2034/742; A61B 2034/743; A61B 2034/744; A61B 2090/0811; A61B 2090/0812; A61B 2090/0813; A61B 34/25; A61B 34/35; A61B 34/70; A61B 34/74; A61B 34/76; A61B 46/10; A61B 46/40; A61B 90/06; A61B 90/361; A61B 90/40; A61B 34/30–34/37; B25J 15/0466; B29C 45/0053; B29C 65/02; B29L 2031/7546; G01V 8/16; Y10S 901/41; Y10S 901/46; Y10S 901/47; Y10S 901/49
See application file for complete search history.

(56) References Cited

U.S. PATENT DOCUMENTS

| | | | |
|---|---|---|---|
| 6,331,181 B1 | 12/2001 | Tierney et al. | |
| 7,048,745 B2 | 5/2006 | Tierney et al. | |
| 9,478,882 B1 | 10/2016 | Schmidt et al. | |
| 9,687,312 B2* | 6/2017 | Dachs, II | A61B 90/98 |
| 2002/0032451 A1 | 3/2002 | Tiernet et al. | |
| 2002/0032452 A1 | 3/2002 | Tierney et al. | |
| 2004/0049205 A1 | 3/2004 | Lee et al. | |
| 2006/0191138 A1 | 8/2006 | Takashima et al. | |
| 2007/0142824 A1 | 6/2007 | Devengenzo | |
| 2007/0151390 A1 | 7/2007 | Blumenkranz et al. | |
| 2008/0103491 A1 | 5/2008 | Omori et al. | |
| 2008/0140088 A1 | 6/2008 | Orban, III | |
| 2009/0024145 A1 | 1/2009 | Meade et al. | |
| 2009/0248039 A1 | 10/2009 | Cooper et al. | |
| 2010/0170519 A1 | 7/2010 | Romo et al. | |
| 2010/0331858 A1 | 12/2010 | Simaan et al. | |
| 2011/0124035 A1 | 5/2011 | Broadley et al. | |
| 2012/0132450 A1 | 5/2012 | Timm et al. | |
| 2012/0209291 A1 | 8/2012 | Anderson et al. | |
| 2012/0230060 A1 | 9/2012 | Tanaka et al. | |
| 2012/0239060 A1* | 9/2012 | Orban, III | A61B 34/30 606/130 |
| 2012/0253330 A1 | 10/2012 | Ries | |
| 2013/0310866 A1 | 11/2013 | Belagali | |
| 2013/0345732 A1 | 12/2013 | Dannaher et al. | |
| 2014/0001231 A1* | 1/2014 | Shelton, IV | A61B 17/07207 227/175.3 |
| 2014/0128886 A1* | 5/2014 | Holop | A61B 18/14 606/130 |
| 2014/0148808 A1 | 5/2014 | Bryant et al. | |
| 2015/0202009 A1 | 7/2015 | Nussbaumer et al. | |
| 2015/0230871 A1 | 8/2015 | Sayler et al. | |
| 2015/0245873 A1 | 9/2015 | Hong et al. | |
| 2015/0257841 A1 | 9/2015 | Dachs, II | |
| 2015/0305815 A1 | 10/2015 | Holop et al. | |
| 2016/0000449 A1 | 1/2016 | Aman et al. | |
| 2016/0058513 A1* | 3/2016 | Giorgi | A61V 34/30 606/130 |
| 2016/0121143 A1 | 5/2016 | Mumaw et al. | |
| 2016/0206391 A1 | 7/2016 | Deodhar | |
| 2016/0317759 A1 | 11/2016 | Lorberbaum et al. | |
| 2016/0361049 A1 | 12/2016 | Dachs et al. | |
| 2016/0361127 A1* | 12/2016 | Dachs, II | A61B 90/361 |
| 2017/0082806 A1 | 3/2017 | Van der Mark et al. | |
| 2018/0168763 A1 | 6/2018 | Scheib et al. | |

FOREIGN PATENT DOCUMENTS

| | | |
|---|---|---|
| JP | 2007-167643 A | 7/2007 |
| JP | 2009-524491 | 7/2009 |
| JP | 2011-516120 A | 5/2011 |
| JP | 2014-512876 A | 5/2014 |
| JP | 2017-512528 A | 5/2017 |
| JP | 2017-512561 A | 5/2017 |
| WO | WO2011037394 A2 | 3/2011 |
| WO | WO2015023834 A1 | 2/2015 |
| WO | 2015/142792 A1 | 9/2015 |
| WO | WO2015150149 A1 | 10/2015 |

OTHER PUBLICATIONS

International Preliminary Report on Patentability dated Jun. 25, 2019, for related PCT Appln. No. PCT/US2017/067320 8 Pages.
U.S. Patent Application filed Dec. 20, 2017, by Scheib et al., U.S. Appl. No. 15/849,450.
U.S. Patent Application filed Dec. 20, 2017, by Scheib et al., U.S. Appl. No. 15/849,443.
U.S. Patent Application filed Dec. 20, 2017, by Scheib et al., U.S. Appl. No. 15/849,429.
U.S. Patent Application filed Dec. 20, 2017, by Scheib et al., U.S. Appl. No. 15/849,419.
U.S. Patent Application filed Dec. 19, 2017, by Scheib et al., U.S. Appl. No. 15/847,638.
U.S. Patent Application filed Dec. 19, 2017, by Scheib et al., U.S. Appl. No. 15/847,518.
Outgoing Written Opinion of the ISA dated May 8, 2018 for WO Application No. PCT/US17/067320.
Outgoing—ISA/210—International Search Report dated May 8, 2018 for WO Application No. PCT/US17/067320.
ISA/220—Notification of Transmittal or Search Report and Written Opinion of the ISA, or the Declaration dated May 8, 2018 for WO Application No. PCT/US17/067320.
ISA/206—Invitation to Pay Additional Fees dated Mar 16, 2018 for WO Application No. PCT/US17/067320.

(56) References Cited

OTHER PUBLICATIONS

Australian Examination Report dated Jun. 18, 2019, for related Australian Appln. No. 2017379816 3 Pages.
Office action dated Dec. 11, 2019 for related U.S. Appl. No. 15/847,518.
Australian Examination Report of the Australian Patent Office dated Jun. 18, 2019, for related Australian Patent Application No. 2017379917.
Communication pursuant to Rules 70(2) and 70a(2) EPC of the European Patent Office dated Jun. 3, 2020 for related European Patent Application No. 17885280.2.
Examination Report of the Australian Patent Office dated Jun. 30, 2020 for related Australian Patent Application No. 2020200350.
Extended European Search Report of the European Patent Office dated May 12, 2020 for related European Patent Application No. 17885280.2.
Final Office Action of the US Patent Office dated Mar. 23, 2020 for related U.S. Appl. No. 15/849,419.
Non Final Office Action of the US Patent Office dated Nov. 29, 2019 for related U.S. Appl. No. 15/849,450.
Notice of Allowance of the US Patent Offfice dated Mar. 10, 2020 for related U.S. Appl. No. 15/849,450.
Notice of Reasons for Refusal of the Japanese Patent Office dated May 20, 2020 for related Japanese Patent Application No. 2019-529616.
Search Report of the Chinese Patent Office dated Apr. 23, 2020 for related Chinese Patent Application No. 201780004183.6.
Search Report of the Japanese Patent Office dated Apr. 1, 2020 for related Japanese Patent Application No. 2019-529616.
First Office Action of the China National Intellectual Property Administration dated May 7, 2020 for related Chinese Patent Application No. 201780004183.6.
Communication pursuant to Rule 164(1) EPC and partial supplementary European search report of the European Patent Office dated Jun. 15, 2020, for related European Patent Application No. 17885373.5.
Notice of Reasons for Rejection of the Japanese Patent Office dated Jun. 2, 2020 for related Japanese Patent Application No. 2019-529255.
Examiner's Report of the Canadian Patent Office dated Jun. 15, 2020 for Canadian Patent Application No. 3,043,933.
Notice of Office Action dated Oct. 30, 2020, for Korean Patent Application No. 10-2019-7017038.
Decision of Refusal of the Japanese Patent Office dated Dec. 8, 2020 for related Japanese Patent Application No. 2019-529255.
Examination report of the Australian Patent Office dated Nov. 21, 2020 for related Australian Patent Application No. 2020203096.
Notification of Reason for Refusal of the Korean Patent Office dated Oct. 30, 2020 for related Korean Patent Application No. 10-2019-7017032.

* cited by examiner

First Configuration

Second Configuration

First Configuration

Second Configuration

SENSORS FOR DETECTING STERILE ADAPTER AND TOOL ATTACHMENT FOR USE IN A ROBOTIC SURGICAL SYSTEM

CROSS-REFERENCE TO RELATED APPLICATIONS

This application claims priority to U.S. Patent Application Ser. No. 62/436,957, filed on Dec. 20, 2016, and to U.S. Patent Application Ser. No. 62/436,965, filed on Dec. 20, 2016, and to U.S. Patent Application Ser. No. 62/436,974, filed on Dec. 20, 2016, and to U.S. Patent Application Ser. No. 62/436,981, filed on Dec. 20, 2016, the content of each of which is hereby incorporated by reference in its entirety.

TECHNICAL FIELD

This invention relates generally to robotic surgical systems, including but not limited to sterile adapters for creating a sterile barrier around portions of a robotic surgical system.

BACKGROUND

Minimally-invasive surgery (MIS), such as laparoscopic surgery, involves techniques intended to reduce tissue damage during a surgical procedure. For instance, laparoscopic procedures typically involve creating a number of small incisions in the patient (e.g., in the abdomen), and introducing one or more tools and at least one camera through the incisions into the patient. The surgical procedures are then performed using the introduced tools, with the visualization aid provided by the camera. Generally, MIS provides multiple benefits, such as reduced patient scarring, less patient pain, shorter patient recovery periods, and lower medical treatment costs associated with patient recovery.

MIS may be performed with non-robotic or robotic systems. Conventional robotic systems, which may include robotic arms for manipulating tools based on commands from an operator, may provide many benefits of MIS while reducing demands on the surgeon. Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

Similar to traditional surgical procedures, it is important to maintain a sterile environment in the surgical field during robotic MIS. However, various components (e.g., motors, encoders, sensors, etc.) of the tool driver and other aspects of the robotic surgical system generally cannot practically be sterilized using conventional sterilization methods such as heat. One solution to maintain sterility is to provide a sterile barrier between the tool driver (and other system components that may appear in the surgical field such as robotic arms, etc.) and the surgical tool, thereby providing a "non-sterile" side for the tool driver and a "sterile" side for the surgical tool. However, the sterile barrier generally should not interfere with how the tool driver actuates the surgical tool. Furthermore, as a tool driver may need to actuate different surgical tools throughout a surgical procedure, the sterile barrier may facilitate simple and efficient exchange or swapping of surgical tools on a tool driver, without compromising the sterile barrier. Proper engagement and attachment of a surgical tool to a tool driver may aid in forming a sterile barrier. Thus, it may be desirable to provide additional systems, devices, and method related to sterile adapters for use in robotic surgery.

SUMMARY

Described herein are systems, devices, and methods for determining one or more attachment states between a tool driver, sterile adapter, and surgical tool for control of a robotic surgical system to aid in proper engagement of the sterile adapter to the system and formation of a sterile barrier. These systems and methods may also be used to communicate a state of the sterile barrier and operation of the robotic surgical system to help an operator and/or other users efficiently understand the attachment and engagement states of the system. Systems and methods as described herein may be used to guide an operator in performing sterile adapter and surgical tool engagement, instead of, for example, depending on the operator to manually confirm proper attachment among a sterile adapter, surgical tool, and tool driver.

Generally, the systems and methods described herein for use in a robotic surgical system may use a tool driver configured to couple to a sterile adapter and a surgical tool. The tool driver may include at least one sterile adapter sensor and surgical tool sensor configured to generate at least one sensor signal corresponding to an attachment state (e.g., presence, engagement, attachment, disengagement, detachment, absence, etc.) between one or more of the tool driver, sterile adapter, and surgical tool. A controller may be coupled to the tool driver, and the controller may include a processor and a memory. In some variations, the controller may be configured to receive at least one sensor signal and generate attachment data using the sensor signal. The attachment data may include at least one attachment state between the tool driver, the sterile adapter, and a surgical tool. The tool driver may be controlled using the attachment data. One or more steps in forming the sterile barrier may be automatically performed by the system based on the attachment data generated from the sensor signals. These features may, for example, improve a surgical tool switching process and reduce operator error in forming a sterile barrier by ensuring that a proper attachment sequence is followed for engaging the sterile adapter and surgical tool to the tool driver. In some variations, the surgical tool may be actuated by the tool driver when complete attachment among the tool driver, the sterile adapter, and the surgical tool has been determined, or the surgical tool may be inhibited from actuation by the tool driver when one or more system components is not sensed and/or is improperly attached.

In some variations, a robotic surgical system may include a tool driver comprising a first housing configured to attach to a surgical tool via a sterile adapter. The first housing may comprise at least one projection extending from a surface of the first housing and be configured to bias away from the surface. The projection may comprise at least one first surgical tool sensor configured to generate a sensor signal comprising at least one attachment state between the tool driver and the surgical tool. At least one rotatable output drive may be supported by the first housing and be configured to communicate torque to an input drive of the surgical tool through the sterile adapter.

In some variations, the first surgical tool sensor may comprise a proximity sensor comprising a magnet coupled to a first end of the projection and a magnetic field transducer coupled to a second end of the projection. The projection may be disposed between a pair of the rotatable output drives. The first housing may comprise a plurality of the projections arranged in a bilaterally symmetrical arrangement. The projection may comprise a compliant material. The projection may comprise at least one of a coil spring and a leaf spring. A second surgical tool sensor may be disposed at a distal end of the first housing. In some of these variations, the second surgical tool sensor may comprise a proximity sensor comprising a magnetic field transducer.

In some variations, a surgical tool may comprise a second housing configured to attach to the sterile adapter. The second housing may comprise a sterile adapter engagement feature comprising a magnetic projection. At least one input drive may be supported by the second housing and configured to receive the torque communicated from an output drive of the tool driver through the sterile adapter. An end effector may extend from the second housing and be operatively coupled to the input drive. In some of these variations, the magnetic projection may comprise a first tapered surface and a second tapered surface opposite the first tapered surface. In some of these variations, a distal end of the surgical tool may comprise the sterile adapter engagement feature.

In some variations, a tool driver for use in a robotic surgical system may comprise a housing configured to couple to a sterile adapter. The housing may comprise a sterile adapter engagement feature mateable with a corresponding tool driver engagement feature on the sterile adapter, and a sterile adapter sensor configured to generate a sensor signal when the tool driver engagement feature is mated with its corresponding sterile adapter engagement feature. At least one rotatable output drive may be supported by the housing and configured to communicate torque to an input drive of a surgical tool through the sterile adapter.

In some variations, a distal end of the housing may comprise the sterile adapter engagement feature and the sterile adapter sensor. The sterile adapter engagement feature may comprise one or more of a recess and a projection. The sterile adapter sensor may be configured to generate the sensor signal when the tool driver engagement feature contacts the sterile adapter sensor.

In some variations, one or more of a tool driver, sterile adapter, and surgical tool may comprise respective housings each including an optical waveguide configured to visually communicate an attachment state among the tool driver, sterile adapter, and surgical tool to an operator. Furthermore, a tool driver may include an illumination source coupled to an optical waveguide configured to propagate light to a sterile adapter and surgical tool. Attachment of the tool driver, sterile adapter, and surgical tool to each other may mechanically couple their corresponding optical waveguides together such that light generated by the tool driver may be output by the optical waveguide of the surgical tool via propagation through the tool driver and sterile adapter. These features may provide an operator an intuitive indication of the attachment state of the surgical system to aid in efficient tool switching and sterile barrier formation.

In some variations, a tool driver may include one or more surgical tool sensors configured to generate at least one sensor signal corresponding to an attachment state between the tool driver and a surgical tool. For example, a surgical tool sensor may be disposed in one or more biasing pegs or other projections in the tool driver, where the one or more biasing pegs may be configured to contact a sterile adapter and urge at least a portion of the peg away from the tool driver and toward a surgical tool. The surgical tool sensor may be disposed in a predetermined portion of the biasing peg and be configured to generate the sensor signal. The sensor signal may be transmitted to a controller for processing and analysis (e.g., to determine the attachment state between the tool driver and the surgical tool). Additionally or alternatively, a surgical tool may include at least one sterile adapter engagement feature comprising a magnetic projection configured for aiding attachment of the surgical tool to the sterile adapter. The magnetic projection may be sensed by another surgical tool sensor to generate the sensor signal. In some variations, a tool driver may include at least one sterile adapter sensor configured to generate a sensor signal when one or more engagement features on each of the sterile adapter and the tool driver mate.

In some variations, a robotic surgical system may include a tool driver comprising a first housing configured to attach to a surgical tool via a sterile adapter. The first housing may comprise at least one projection extending from a surface of the first housing and be configured to bias away from the surface. The projection may comprise at least one first surgical tool sensor configured to generate a sensor signal comprising at least one attachment state between the tool driver and the surgical tool. At least one rotatable output drive may be supported by the first housing and be configured to communicate torque to an input drive of the surgical tool through the sterile adapter.

In some variations, the first surgical tool sensor may comprise a proximity sensor comprising a magnet coupled to a first end of the projection and a magnetic field transducer coupled to a second end of the projection. The projection may be disposed between a pair of the rotatable output drives. The first housing may comprise a plurality of the projections arranged in a bilaterally symmetrical arrangement. The projection may comprise a compliant material. The projection may comprise at least one of a coil spring and a leaf spring. A second surgical tool sensor may be disposed at a distal end of the first housing. In some of these variations, the second surgical tool sensor may comprise a proximity sensor comprising a magnetic field transducer.

In some variations, a surgical tool may comprise a second housing configured to attach to the sterile adapter. The second housing may comprise a sterile adapter engagement feature comprising a magnetic projection. At least one input drive may be supported by the second housing and be configured to receive the torque communicated from an output drive of the tool driver through the sterile adapter. An end effector may extend from the second housing and be operatively coupled to the input drive.

In some variations, the magnetic projection may comprise a first tapered surface and a second tapered surface opposite the first tapered surface. In some of these variations, a distal end of the surgical tool comprises the sterile adapter engagement feature.

In some variations, a tool driver for use in a robotic surgical system may comprise a housing configured to couple to a sterile adapter. The housing may comprise a sterile adapter engagement feature mateable with a corresponding tool driver engagement feature on the sterile adapter, and a sterile adapter sensor configured to generate a sensor signal when the tool driver engagement feature is mated with its corresponding sterile adapter engagement feature. At least one rotatable output drive may be supported by the housing and be configured to communicate torque to an input drive of a surgical tool through the sterile adapter. In some of these variations, a distal end of the housing may comprise the sterile adapter engagement feature and the sterile adapter sensor. The sterile adapter engagement feature may comprise one or more of a recess and a projection. The sterile adapter sensor may be configured to generate the sensor signal when the tool driver engagement feature contacts the sterile adapter sensor.

In some variations, the respective housings of the tool driver and surgical tool may define portions to support respective electronic communication devices that may lie in close proximity to each other when the surgical tool is attached to the sterile adapter and tool driver. Close proximity between the electronic communication devices may reduce signal interference, improve power efficiency, and enable wireless power transfer between electronic devices disposed within the tool driver and surgical tool. For example, an electronic communication device of the tool driver may be in a same plane as a rotatable output drive disk of the tool driver. A corresponding electronic communication device of the surgical tool may be disposed in a projection of a surgical tool housing on a side facing the tool driver. When the tool driver, sterile adapter, and surgical tool are attached to each other, a distance between the electronic communication devices may be reduced, if not minimized, in order to improve one or more of signal-to-noise ratio (SNR) and power transfer efficiency.

In some variations, a robotic surgical system may include a tool driver comprising a first housing configured to attach to a surgical tool via a sterile adapter. At least one output drive may be coupled to a corresponding rotatable output drive disk each supported by the first housing. The output drive may be configured to communicate torque to an input drive of the surgical tool through the sterile adapter. A first electronic communication device may be configured to wirelessly communicate with the surgical tool and disposed substantially in a plane of the output drive disk.

In some variations, the surgical tool may comprise a second housing configured to couple to the sterile adapter. The second housing may comprise a projection and a second electronic communication device configured to wirelessly communicate with the tool driver. The second electronic communication device may be disposed in the projection. An end effector may extend from the second housing and be operatively coupled to the input drive. The input drive may be supported by the second housing and configured to receive torque communicated from the output drive of the tool driver through the sterile adapter.

In some variations, the sterile adapter may comprise a frame configured to be interposed between the tool driver and the surgical tool. A plate assembly may be coupled to the frame. The frame may comprise a communication portion configured to support the projection of the surgical tool substantially in a plane of the plate assembly when the surgical tool is attached to the sterile adapter and the plate assembly is biased toward the tool driver. At least one rotatable coupler may be supported by the plate assembly and configured to communicate torque from the output drive of the tool driver to the input drive of the surgical tool.

A proximal end of the first housing may be configured to support the first electronic communication device. In some of these variations, a proximal end of the surgical tool may comprise the projection. In some of these variations, a proximal end of the frame may comprise the communication portion.

BRIEF DESCRIPTION OF THE DRAWINGS

FIG. 3A is a perspective view of a tool driver, FIG. 3B is a perspective view of a sterile adapter coupled to the tool driver, and FIG. 3C is a perspective view of a surgical tool coupled to the sterile adapter and tool driver.

FIG. 4A is a plan view of the tool driver. FIGS. 4B-4C are cross-sectional side views of the tool driver depicted in FIG. 4A. FIGS. 4D-4E are detailed cross-sectional side views of respective FIGS. 4B-4C.

FIG. 5A is a plan view of the tool driver. FIG. 5B is a cross-sectional side view of the tool driver depicted in FIG. 5A. FIG. 5C is a detailed cross-sectional side view and a portion of a surgical tool and the tool driver depicted in FIG. 5B.

FIG. 6A is a cross-sectional side view of one variation of a sterile adapter and surgical tool. FIG. 6B is a detailed cross-sectional side view of another variation of a sterile adapter and surgical tool.

FIG. 7A is a plan view of the tool driver coupled to a sterile adapter, FIG. 7B is a cross-sectional side view of the tool driver and sterile adapter depicted in FIG. 7A, and FIG. 7C is a detailed cross-sectional side view of the tool driver and sterile adapter depicted in FIG. 7B.

DETAILED DESCRIPTION

Figure 1:
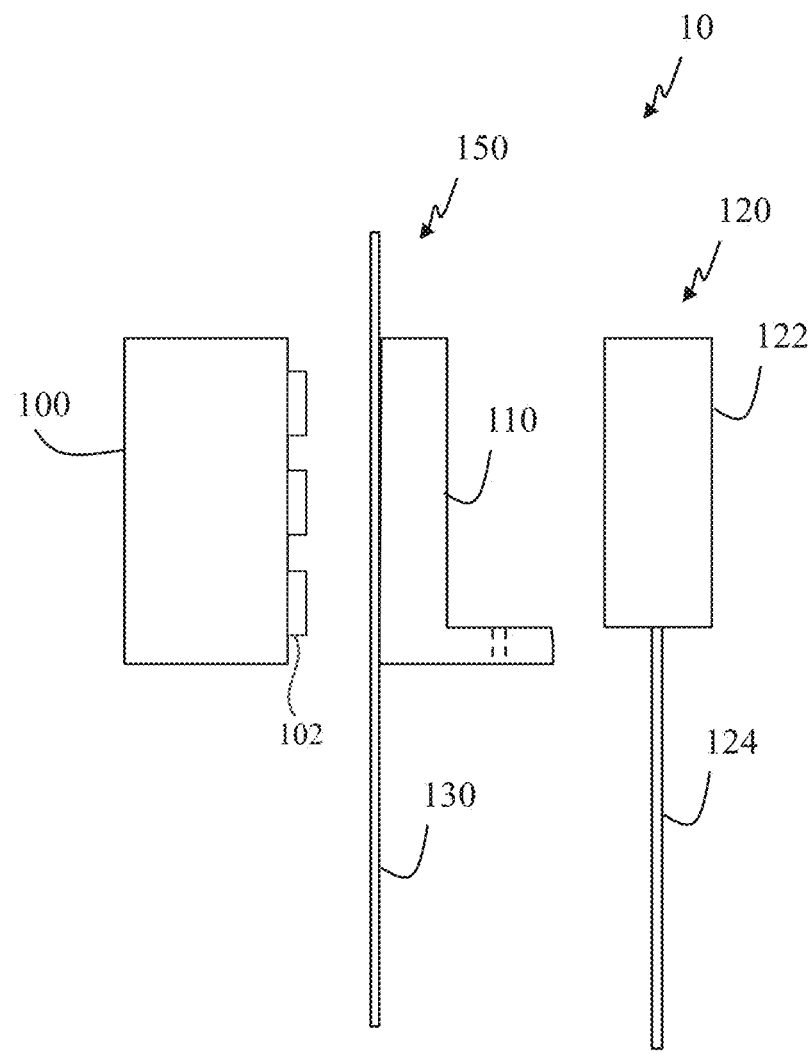
FIG. 1 is an illustrative schematic of a portion of a robotic surgical system depicting a tool driver, sterile adapter, sterile barrier, and surgical tool.

Described here are systems, devices, and methods for controlling a robotic surgical system using a tool driver, sterile adapter, and surgical tool. As shown generally in the schematic of FIG. 1, a robotic surgical system (10) may comprise a tool driver (100) configured to actuate a surgical tool (120). One or more drive outputs (102) of the tool driver (100) may, for example, actuate one or more drive inputs (not shown) on a proximal portion (122) of the surgical tool (120), thereby causing movement (e.g., grasping, cutting) of an end effector (not shown) located at a distal end of a tool shaft (124). Additionally, a sterile barrier (150) may be placed between the tool driver (100) and the surgical tool (120), forming a barrier between an interior, non-sterile side including the tool driver (100) and an exterior, sterile side including the surgical tool (120) which may, for example, be located at a sterile surgical site. The sterile barrier (150) may, for example, include a sterile drape (130) configured to cover at least the tool driver (100), and a sterile adapter (110) coupled to the sterile drape (130) and located between the tool driver (100) and the surgical tool (120). The sterile adapter (110) may be configured to communicate or otherwise transmit an actuation force (e.g., rotary torque, linear movement) from at least one drive output (102) of the tool driver (100) to at least one drive input of the surgical tool (120). Examples of tool drivers (100), sterile adapters (110), and surgical tools (120) are described in more detail herein.

Generally, the systems and methods described herein may include attaching a sterile adapter and a surgical tool to a tool driver. One or more sensors disposed in one or more of the tool driver, sterile adapter, and surgical tool may be configured to generate sensor signals used to monitor and advance the attachment process. For example, attachment of the sterile adapter to the tool driver may be sensed and visually communicated to an operator through color-coded light output from optical waveguides (e.g., light pipe) of one or more of the tool driver and the sterile adapter. Furthermore, upon determination of sterile adapter attachment, the tool driver may be actuated without operator input to fully engage (e.g., attach) the sterile adapter to the tool driver in order to prepare the surgical system for surgical tool attachment. On the other hand, when the sensor detects improper attachment to the tool driver, the operator may be notified of the error through color-coded light output from an optical waveguide of the tool driver. In such situations, the tool driver may be inhibited from operating (e.g., to prevent damage to the system and/or operator). Disengagement and/or detachment of the surgical system may also be sensed and subsequently communicated to an operator (e.g., visually communicated using an optical waveguide). Using sensors to determine an attachment state between the tool driver, sterile adapter, and surgical tool and communicating the attachment state to an operator may, for example, aid in efficiently performing tool switching and proper sterile barrier formation.

In some variations, an attachment state between a tool driver, sterile adapter, and surgical tool may be output by the robotic surgical system to an operator using one or more output modalities. In some variations, one or more of the tool driver, sterile adapter, and surgical tool may include a visual output device for communicating the attachment state to an operator quickly and intuitively. For example, upon attachment of the sterile adapter and/or surgical tool to the tool driver, respective optical waveguides of the attached components may indicate the attachment state. Additionally or alternatively, the surgical system may include other visual output devices such as a user console (e.g., surgeon bridge) and/or display device. The operator may additionally or alternatively receive audio and haptic output from the respective audio and haptic devices.

Attachment state data may be generated using one or more sensor signals. In some variations, a tool driver may include at least one surgical tool sensor configured to generate a sensor signal corresponding to an attachment state between the tool driver and a surgical tool. The sensor signal may be used to generate attachment data. The attachment data may be used to control the tool driver and/or output an attachment state to an operator. In some variations, one or more biased projections (e.g., biasing pegs) may extend from a surface of a tool driver housing. The projection may be biased to contact and urge a portion of a sterile adapter away from a tool driver housing and towards a surgical tool. A first surgical tool sensor (e.g., proximity sensor) may be disposed within the projection and configured to determine an amount of movement of the projection relative to the tool driver housing. An attachment state between the tool driver and surgical tool may be derived from the surgical tool sensor data.

In some variations, a tool driver may include a second surgical tool sensor configured to generate another sensor signal corresponding to attachment between the surgical tool and the sterile adapter to the tool driver. In some variations, the second surgical tool sensor may be a proximity sensor (e.g., magnetic field transducer) configured to detect a magnetic projection of a surgical tool. As other examples, the second surgical tool sensor may include a switch (e.g., that detect physical contact between the surgical tool and/or sterile adapter to the tool), an optical sensor, an inductive sensor, and/or other suitable sensor. An attachment state between the tool driver and surgical tool may be derived from the sensor signal generated from the second surgical tool sensor. In some variations, the magnetic projection may be configured to mate with a corresponding recess in the sterile adapter. The surfaces of the projection may be configured to guide attachment of the surgical tool to the sterile adapter. Thus, the projection may aid in proper alignment and attachment (e.g., seating) of the surgical tool to the sterile adapter.

In some variations, a tool driver may include at least one sterile adapter sensor configured to generate a sensor signal when the sterile adapter is fully attached to the tool driver. For example, the sterile adapter sensor may generate the sensor signal when corresponding engagement features on the tool driver and the sterile adapter make contact and mate. In other examples, the sterile adapter sensor may additionally or alternatively include another suitable sensor (e.g., proximity sensor) for detecting when the sterile adapter is fully attached to the tool driver. The sensor signal may be used to generate attachment data for controlling the tool driver. The sterile adapter sensor may be disposed on a portion of the housing of the tool driver (e.g., distal end) such that improper contact and/or partial attachment of the sterile adapter to the tool driver generates a corresponding sensor signal.

In some variations, the tool driver and surgical tool may include electronic communication devices disposed in a tool driver and surgical tool to communicate tool and system data with each other. The communication devices may be configured to be in close proximity (e.g., within a few millimeters) when the surgical tool is attached to the sterile adapter and tool driver. Close proximity between the electronic communication devices permits reduced signal interference and may enable wireless power transfer between the tool driver and surgical tool. A first electronic communication device of the tool driver may be disposed close to a side of a tool driver housing facing the surgical tool to minimize the distance between the first electronic communication device and the surgical tool. Likewise, a second electronic communication device of the surgical tool may be disposed close to a side of the surgical tool housing facing the tool driver to minimize the distance between the second electronic communication device and the tool driver. The sterile adapter may include a communication portion configured to support the second electronic communication device such that the distance between the surgical tool and tool driver is minimized when the sterile adapter is interposed between them.

I. Methods

Described herein are methods for controlling a robotic surgical system using the systems and devices described herein. Generally, the methods described here include using one or more sensors to generate an attachment state between a surgical tool, sterile adapter, and tool driver. In response to the attachment state, a controller may control operation of the tool driver and output (e.g., notify) the attachment state to an operator. For example, the methods described here may include determining partial attachment of a sterile adapter to a tool driver, and subsequently actuating output drives of the tool driver to fully attach the sterile adapter to the tool driver. The system may notify the attachment state to the operator (e.g., partial attachment, full attachment, partial detachment, full detachment, improper attachment) using one or more of audio, visual and haptic output. Any of the devices and systems as described herein may be used to perform the methods discussed herein. For example, a system may include a tool driver configured to attach to a surgical tool via a sterile adapter. The tool driver may comprise at least one sterile adapter sensor and/or at least one surgical tool sensor. These sensors may be configured to generate at least one sensor signal used to generate an attachment state of the system (e.g., the sterile adapter sensor may be configured to generate a sensor signal corresponding to an attachment state between the tool driver and the sterile adapter, and/or the surgical tool sensor may be configured to generate a sensor signal corresponding to an attachment state between the surgical tool/sterile adapter and the tool driver). A controller comprising a processor and a memory may be coupled to the tool driver and used to control actuation of the tool driver.

Figure 2:
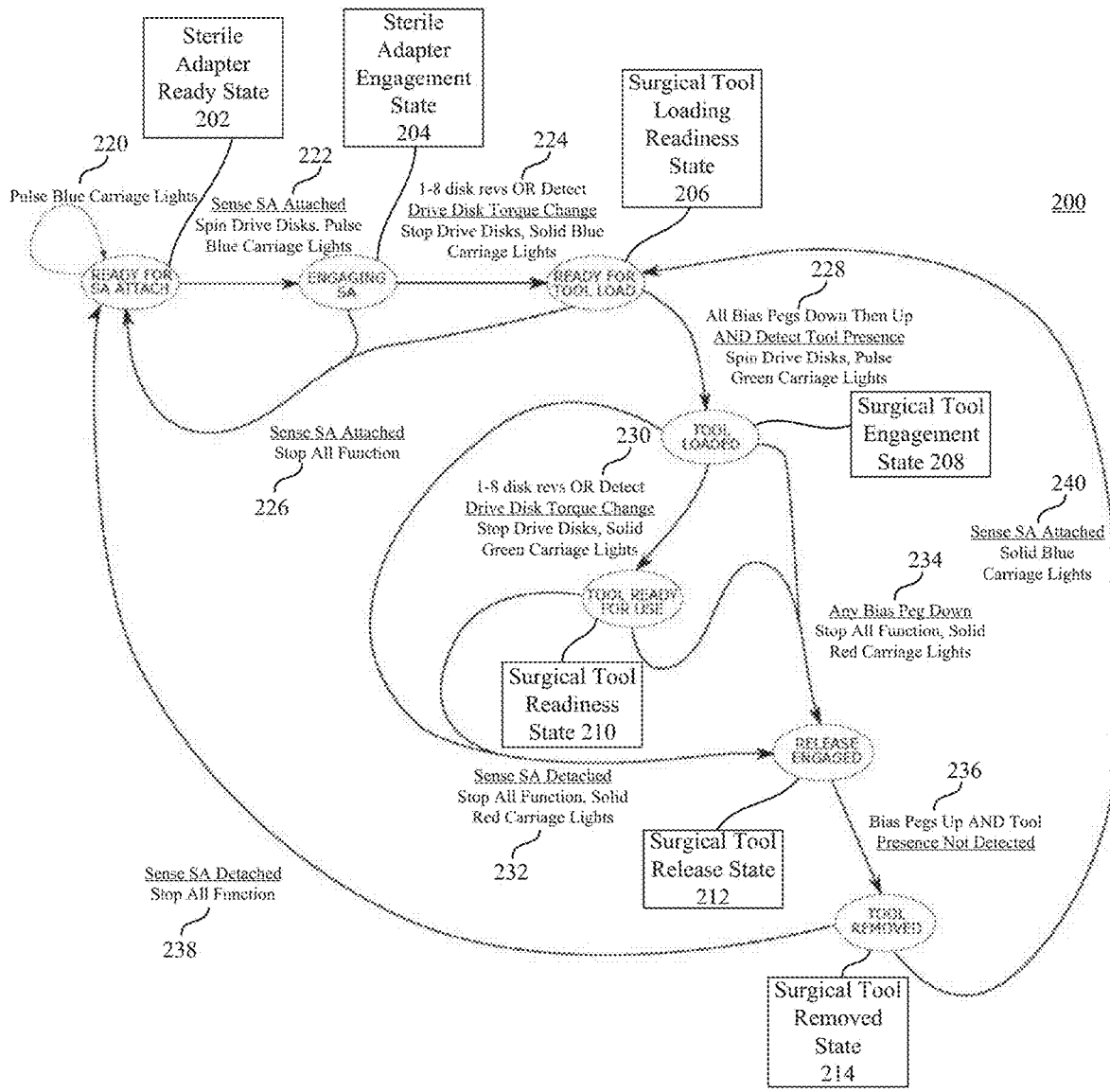
FIG. 2 is an illustrative state diagram for a robotic surgical control system.

Generally, the methods described herein may include receiving the sensor signal generated by one or more sensors of the tool driver and generating attachment data using the sensor signal. For example, a controller may receive and process the sensor signal to generate attachment data. The attachment data may comprise at least one attachment state between the tool driver, the sterile adapter, and the surgical tool. Tool driver operation and/or operator notification may be based on the attachment data. The methods described herein may, for example, aid proper engagement of a surgical tool and sterile adapter to the tool driver for formation of a sterile barrier. This may have one or more benefits, such as efficient tool switching and sterile barrier formation, as well as increased safety as the system need not rely on operator confirmation of an attachment state. FIG. 2 is a state diagram that describes an illustrative method of controlling a system as described herein. Of course, the exemplary variation described in FIG. 2 is provided for the sake of illustrative description and is non-limiting.

Figure 3A:
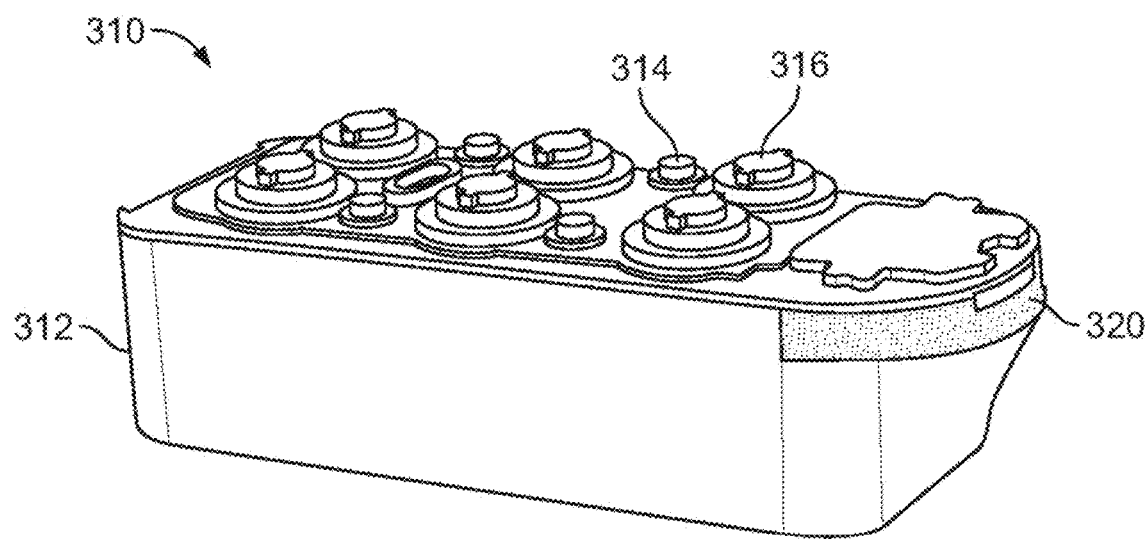
FIGS. 3A-3C are perspective views of a variation of a robotic surgical system depicting one or more of a tool driver, sterile adapter, and surgical tool.
Figure 3B:
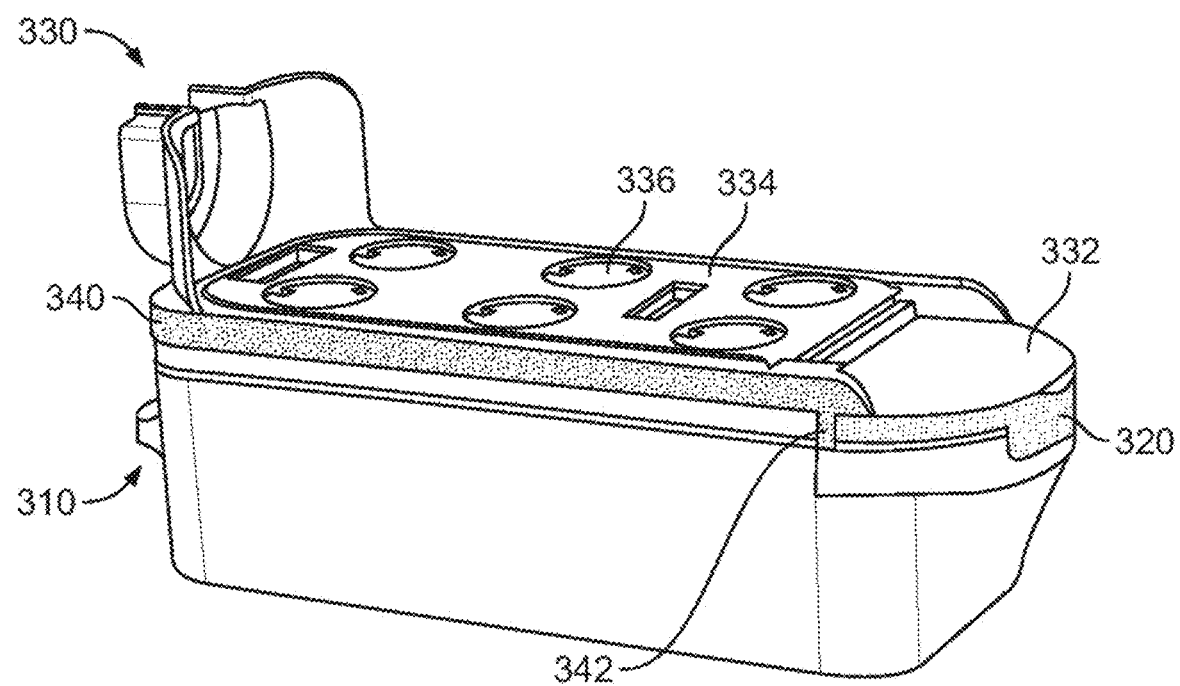
Figure 3C:
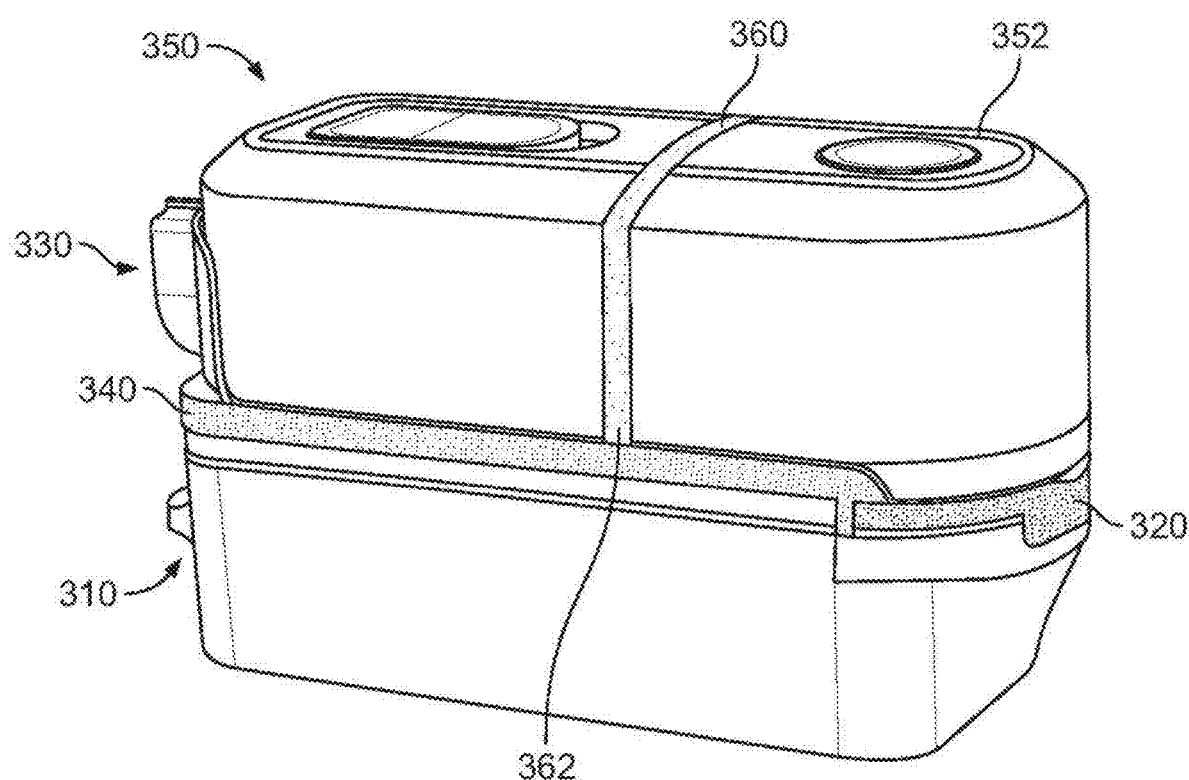

In some variations, the attachment state of the system may be communicated to the operator using one or more output methods (e.g., described in detail with respect to FIGS. 3A-3C). For example, a status of the system may be communicated to the operator using a set of light patterns emitted from respective optical waveguides (e.g., light pipe) of one or more of the tool driver, sterile adapter, and surgical tool. The light patterns described herein may, for example, comprise one or more of flashing light, occulting light, isophase light, etc., and/or light of any suitable light/dark pattern. For example, flashing light may correspond to rhythmic light in which a total duration of the light in each period is shorter than the total duration of darkness and in which the flashes of light are of equal duration. Occulting light may correspond to rhythmic light in which the duration of light in each period is longer than the total duration of darkness. Isophase light may correspond to light which has dark and light periods of equal length. Light pulse patterns may include one or more colors (e.g., different color output per pulse), light intensities, and frequencies. Variations of optical waveguides of the system are described in further detail herein. In some variations, one or more of visual, audible, and haptic output may be provided to an operator to communicate an attachment state of the system.

As another example, the attachment state of the system may additionally or alternatively be visually communicated to the operator using a display device. Variations of display devices of the system are described in further detail herein and may comprise, for example, one or more of an LED display, touch screen display, user console, virtual reality headset, and other suitable displays.

As another example, the attachment state of the system may additionally or alternatively be audibly communicated using an audio device. Variations of audio devices of the system are described in further detail herein and may comprise, for example, one or more of a speaker, user console, virtual reality headset, and other suitable audio devices.

As yet another example, the attachment state of the system may additionally or alternatively be haptically communicated using a haptic device. Variations of haptic devices of the system are described in further detail herein and may comprise, for example, a vibrational motor in at least one of the tool driver, distal portion of the arm, input device (e.g., hand-held controller), and other suitable haptic devices.

Sterile Adapter Ready State

In some variations, the control process (200) may include a sterile adapter ready state (202) in which both a sterile adapter and surgical tool are fully detached from a tool driver. One or more surgical tool sensors (e.g., described in detail with respect to FIGS. 4D-4E and 6B) may output a sensor signal corresponding to a detachment state between the tool driver and a surgical tool. A sterile adapter attachment sensor (e.g., described in detail with respect to FIG. 7C) may output a sensor signal corresponding to a detachment state between the tool driver and a sterile adapter. Consequently, the tool driver may be inhibited from driving an output drive in the sterile adapter ready state (202) based on these sensor signals.

Referring back to FIG. 2, a tool driver may output a first light pattern (220) corresponding to the sterile adapter ready state (202). In some variations, the tool driver may output a slow pulse of colored light (e.g., blue light) at a predetermined light intensity using a first optical waveguide of the tool driver (e.g., see FIG. 3A). For example, the first light pattern may comprise pulses of light having a duration of about half a second or more. Additionally or alternatively, a display device may output text or an image indicating that the system is ready for attachment of a sterile adapter to the tool driver. For example, a user console (e.g., surgeon bridge) coupled to the system may display a message to the operator such as "Please attach the sterile adapter to the tool driver" and/or "Ready for sterile adapter attachment." In some variations, the sterile adapter ready state (202) may correspond to a first audio pattern and first haptic pattern that inhibits audio and haptic output. In other variations, an audio device may output a sound effect (e.g., bing, ping, beep, etc.) and/or verbal message at a predetermined time interval to remind an operator to attach a sterile adapter to the tool driver.

Sterile Adapter Engagement State

An operator may at least partially attach a sterile adapter to the tool driver. In response, a controller may determine that the system transitions from a sterile adapter ready state (202) to a sterile adapter engagement state (204) corresponding to partial attachment of the sterile adapter to the tool driver. In some variations, partial attachment of the sterile adapter to the tool driver may mean at least a portion of the sterile adapter may be attached to the tool driver, but at least another portion of the sterile adapter may be detached or disengaged from the tool driver.

Figure 7A:
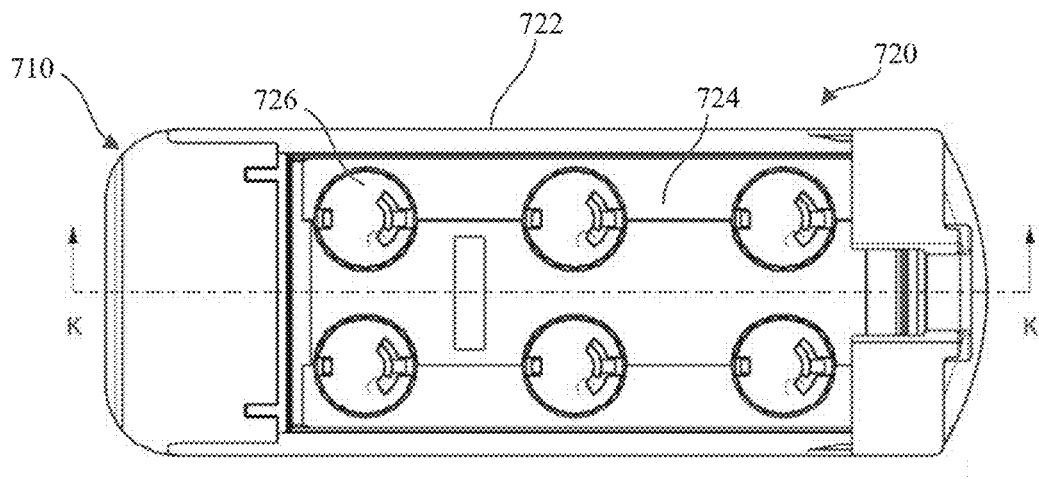
FIGS. 7A-7C are illustrative views of a variation of a tool driver and sterile adapter.
Figure 7B:
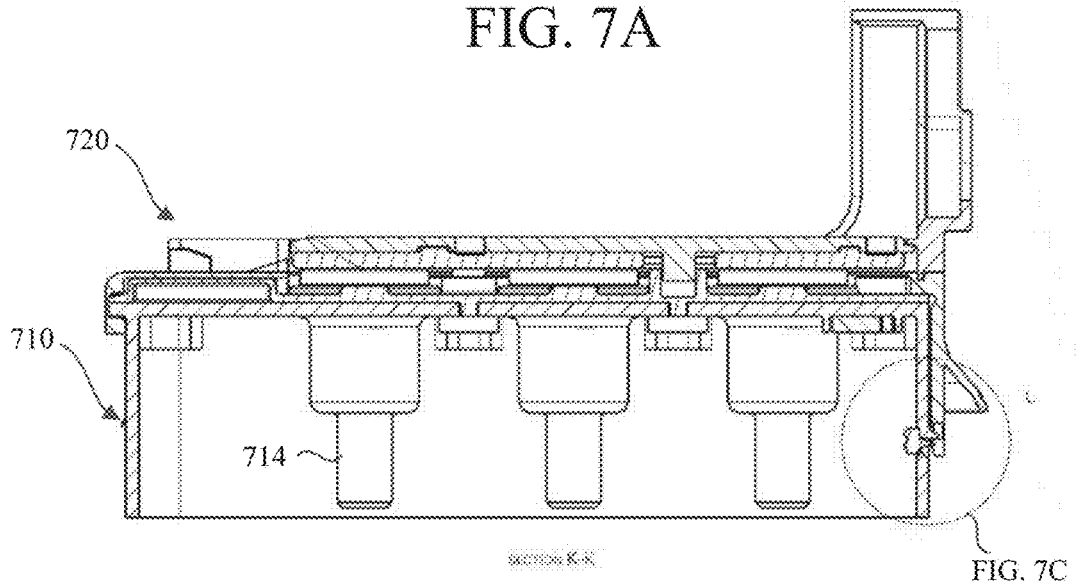

For example, in a variation in which a tool driver includes at least one rotatable output drive (e.g., rotary axis drive), a sterile adapter may include a frame and at least one rotatable coupler configured to transmit torque from the rotatable output drive to a surgical tool. Partial attachment of the sterile adapter to the tool driver may mean the frame may be attached to the tool driver, but at least one rotatable coupler of the sterile adapter may not be operatively coupled with corresponding output drives of the tool driver (and thereby fail to transmit torque). For example, FIGS. 7A-7B illustrate attachment of an exemplary sterile adapter to a tool driver. In some variations, an operator may attach a proximal end of the sterile adapter to the tool driver before attachment of a distal end of the sterile adapter. The system may then determine the transition from the ready state (202) to the engagement state (204) when a sensor signal corresponding to partial attachment of the sterile adapter to the tool driver (222) is generated by a sterile adaptor sensor. One or more surgical tool sensors (e.g., see FIGS. 4D, 4E, and 5C) may generate a sensor signal corresponding to detachment between the surgical tool and the tool driver. This combination of sensor signals may correspond to partial attachment where the sterile adapter is partially attached to the tool driver, but not ready for surgical tool loading (206).

In response to the partial attachment of the sterile adapter to the tool driver (222), a controller of the system may actuate one or more rotatable output drives of the tool driver to physically engage the rotatable output drives of the tool driver to corresponding rotatable couplers of the sterile adapter (224). For example, the sterile adapter may comprise a frame and a plate assembly coupled to the frame. The plate assembly may be configured to have a range of motion perpendicular to a plane of the frame. The plate assembly may comprise at least one rotatable coupler supported by the plate assembly. The rotatable coupler may be configured to communicate the torque output from the output drive of the tool driver. In systems including other variations of tool drivers and sterile adapters, the controller of the system may actuate at least a portion of the tool driver in any suitable manner so as to engage an output drive to a corresponding portion of a sterile adapter. For example, in a system including a tool driver having at least one linear output drive and a sterile adapter having at least one linearly-movable coupler or other interface configured to engage the linear output drive, the controller may actuate the linear output drive (e.g., distally and/or proximally in an axial direction) so as to engage the linear output drive with the linearly-movable coupler.

In some variations, the tool driver may output a second light pattern in response to determining the partial attachment state of the sterile adapter. In some variations, the tool driver may output a fast pulse of colored light (e.g., blue light) at a predetermined light intensity using an optical waveguide of the tool driver. For example, the second light pattern may comprise pulses of light having a duration of less than about half a second (e.g., about ¼ second). In some variations, as further described herein, attachment of the sterile adapter to the tool driver may mechanically couple the optical waveguides (e.g., light pipes) of the sterile adapter and tool driver together such that light emitted by an illumination source of the tool driver may be propagated through and distributed by the optical waveguide of the sterile adapter. The light output by the sterile adapter confirms to the operator that the sterile adapter is attached to the tool driver. This may allow an operator to quickly identify the sterile adapter engagement state (204) by looking at multiple visual indicators (e.g., color, pulse frequency, light distribution, etc.) output by the tool driver and the sterile adapter.

Additionally or alternatively, a display device may output text or an image indicating that the sterile adapter is partially attached to the tool driver in the sterile adapter engagement state (204). For example, a user console coupled to the system may display a message to the operator such as "Sterile adapter detected," "Sterile adapter attached to tool driver," and/or "Engaging sterile adapter disks." In some variations, an audio device may output a second audio pattern corresponding to the sterile adapter engagement state. For example, the audio device may output a set of fast, short bings, or other suitable sound effects at a predetermined frequency and volume for a predetermined length of time. A second haptic pattern may correspond to the sterile adapter engagement state and inhibit haptic output. In other variations, the audio device may output the message displayed by the user console and/or verbally output the operational steps of the tool driver in response to attachment of the sterile adapter (e.g., "Engaging sterile adapter disks").

Conversely, the operator may detach the sterile adapter from the tool driver by, for example, rotationally lifting the sterile adapter off from a distal end of the tool driver. The system may transition from the sterile adapter engagement state (204) to the sterile adapter ready state (202) when a sensor signal from a sterile adaptor sensor is generated that corresponds to detachment between the sterile adapter and the tool driver (226). Likewise, one or more surgical tool sensors may generate a sensor signal corresponding to detachment between the surgical tool and the tool driver. The tool driver may be inhibited from actuating an output drive in the sterile adapter detachment state (226). In some variations, one or more of visual, audio, and haptic output may also be inhibited when detachment of the sterile adapter is sensed (226).

Surgical Tool Loading Readiness State

From the sterile adapter engagement state (204), a controller may determine a transition of the system into a surgical tool loading readiness state (206). For example, the controller may rotate the rotatable output drives of the tool driver for a predetermined number of revolutions in one or more directions (e.g., clockwise, counter-clockwise) to fully attach the sterile adapter to the tool driver. The tool driver and sterile adapter may be in a tool loading readiness state (206) when the rotatable couplers of the sterile adapter are fully physically engaged with their corresponding rotatable output drives of the tool driver. Upon full attachment, torque generated by the output drives may be communicated to the couplers of the sterile adapter. In some variations, the rotatable output drives may rotate until a change in torque is detected in the output drives using one or more torque sensors and rotary encoders. A change in torque may correspond to added resistance from the rotatable couplers that indicate that the rotatable couplers have physically engaged with their corresponding output drives of the tool driver.

In some variations, one or more of the tool driver and sterile adapter may output a third light pattern from the system to notify an operator of the tool loading readiness state (206). In some variations, one or more of the tool driver and sterile adapter may output solid colored light (e.g., blue light) at a predetermined light intensity using an optical waveguide of the tool driver and/or sterile adapter. Additionally or alternatively, a display device may output text or an image indicating that the system is ready for attachment of a surgical tool to the sterile adapter and tool driver. For example, a user console coupled to the system may display a message to the operator such as "Please attach a surgical tool to the tool driver" and/or "Ready for tool loading." In some variations, an audio device may output a third audio pattern corresponding to the tool loading readiness state (206). For example, the audio device may output one or more extended bings (having a duration longer than a short bing) at a predetermined frequency and volume for a predetermined length of time. A third haptic pattern may correspond to the surgical tool loading readiness state and inhibit haptic output. In other variations, the audio device may output the message displayed by the user console and/or verbally describe the actuation of the tool driver in response to the tool loading readiness state (206).

In some circumstances, after attachment of the sterile adapter to the tool driver, an operator may detach the sterile adapter from the tool driver. The system may transition from the tool loading readiness state (206) to the sterile adapter ready state (202) when a sensor signal generated by a sterile adaptor sensor corresponds to detachment of the sterile adapter from the tool driver (226). Likewise, one or more surgical tool sensors may generate a sensor signal corresponding to detachment of a surgical tool from the tool driver.

Surgical Tool Engagement State

Once the sterile adapter is fully attached to the tool driver, an operator may partially attach a surgical tool to the sterile adapter. In response, a controller may determine that the system transitions from the surgical tool loading readiness state (206) to the surgical tool engagement state (208) corresponding to partial attachment of the surgical tool to the sterile adapter (228). In some variations, partial attachment of the surgical tool to the sterile adapter may mean at least a portion of the surgical tool may be attached to the sterile adapter, while another portion of the surgical tool may be detached or disengaged from the sterile adapter. For example, the housing of the surgical tool may be attached to a frame of the sterile adapter to the tool driver, but input drives of the surgical tool may not be operatively coupled with corresponding rotatable couplers of the sterile adapter. The system may then transition from the readiness state (206) to the tool engagement state (208) of a sensor signal corresponding to partial attachment between the surgical tool and the sterile adapter (228) is generated by one or more surgical tool sensors. One or more projections (e.g., biasing pegs) of the tool driver (see e.g., FIGS. 4B-4E and accompanying description herein) may generate a sensor signal corresponding to the projections being pushed downward toward a surface of the tool driver momentarily (as the operator pushes the surgical tool longitudinally over a surface of the sterile adapter). The projections may then bias away from the surface of the tool driver (as the surgical tool becomes seated within the plate assembly of the sterile adapter). For example, a surface of the sterile adapter may comprise mating features (e.g., projections) that create an uneven surface and are configured to mate with corresponding mating features (e.g., recesses) on the sterile adapter. When an operator slides the surgical tool over the sterile adapter, the projections may slide over the surface of the plate assembly unevenly so as to momentarily push the plate assembly downward. When the projections mate into corresponding recesses, the plate assembly may bias back upward.

In some variations, a mating feature of a surgical tool may be used to determine an attachment state of the surgical tool. For example, a second surgical tool sensor (e.g., proximity sensor) disposed on a distal end of the tool driver and facing the sterile adapter may generate a sensor signal corresponding to the presence of the surgical tool when a magnetic projection of the surgical tool is slid into a corresponding recess of the sterile adapter (see e.g., FIGS. 6A-6B and accompanying description herein). For example, the output of the second surgical tool sensor may indicate that the surgical tool is attached to and fully seated in the sterile adapter so as to be ready for input drive coupling.

In some variations, a tool driver may further comprise a sterile adapter sensor configured to generate a sensor signal corresponding to an attachment state between the tool driver and the sterile adapter. For example, as further described herein with reference to FIGS. 7A-7C, in some variations, a distal end of the sterile adapter may be mechanically latched to the tool driver to engage with the sterile adapter sensor. The combination of these surgical tool and sterile adapter sensor signals may be used by a controller to transition the system from the tool loading readiness state (206) to the tool engagement state (208).

In some variations, the tool driver and surgical tool may each comprise respective electronic communication devices such as wireless communication devices configured to communicate with each other and/or transfer power wirelessly when they are in close proximity (e.g., within a few centimeters). Attachment of the surgical tool to the sterile adapter and the tool driver may correspond to the electronic communication devices becoming within a predetermined range of each other. An exemplary arrangement with such respective electronic communication devices is described below with reference to FIG. 8.

In response to the tool engagement state (208), a controller of the system may actuate one or more rotatable output drives of the tool driver to physically engage the rotatable output drives of the tool driver with corresponding rotatable input drives of the surgical tool. In some variations, the tool driver may output a fourth light pattern in response to the partial attachment state of the surgical tool. In some variations, one or more of the tool driver, sterile adapter, and surgical tool may output a fast pulse of colored light (e.g., green light) at a predetermined light intensity using one or more optical waveguides of the tool driver, sterile adapter, and surgical tool. For example, the fourth light pattern may comprise pulses of light having a duration of less than about half a second (e.g., about ¼ second). In some variations, attaching the surgical tool to the sterile adapter may mechanically couple the waveguides of the surgical tool, sterile adapter, and the tool driver together such that light generated by the tool driver may be propagated to and distributed by the optical waveguides of the sterile adapter and/or surgical tool. This may allow an operator to quickly confirm the tool engagement state (208) between the tool driver and the surgical tool by simply looking at which system component is emitting light.

Additionally or alternatively, a display device may output text or an image indicating that the surgical tool is partially attached to the tool driver in the tool engagement state (208). For example, a user console coupled to the system may display a message to the operator such as "Surgical tool detected," "Surgical tool attached to tool driver," and/or "Engaging surgical tool input drives." In some variations, an audio device may output a fourth audio pattern corresponding to the tool engagement state (208). For example, the audio device may output a set of fast, short bings at a predetermined frequency (e.g., different from the frequency of the second audio pattern) and predetermined volume for a predetermined length of time. A haptic device may output a fourth haptic pattern corresponding to the tool engagement state (208). For example, a haptic device of one or more of the tool driver and surgical tool may output a small vibration. In other variations, the audio device may output the message displayed by the user console and/or verbally describe the actuation of the tool driver in response to surgical tool attachment (e.g., actuation of one or more output drives). In some variations, the electronic communication device (e.g., wireless communication device) of the surgical tool in the tool engagement state may transmit tool functionality and other data (e.g., security data, utilization data, diagnostic data, manufacturing data, etc.) to the electronic communication device of the tool driver. In turn, the electronic communication device of the surgical tool may receive authentication data and/or other data (calibration data, usage data, log data, surgical system data, patient data, procedure data, regulatory data, etc.) that may be stored in a memory of the surgical tool.

Surgical Tool Readiness State

A controller may control a system in the tool engagement state (208) to transition (230) into a surgical tool readiness state (210) that corresponds to a full attachment state between the surgical tool, sterile adapter, and tool driver. For example, a tool driver may rotate the rotatable output drives for a predetermined number of revolutions in one or more directions (e.g., clockwise, counter-clockwise) to fully seat the surgical tool in the sterile adapter. The surgical tool in the tool readiness state (210) may then be actuated via the tool driver to operate the surgical tool under operator guidance. The tool driver and surgical tool may be in a tool readiness state (210) when the rotatable input drives of the surgical tool are fully physically engaged (e.g., fully attached) with their corresponding rotatable output drives of the tool driver. When the surgical tool is fully attached (e.g., fully seated), torque generated by the output drives may be communicated to the input drives of the tool driver. In some variations, the rotatable output drives may rotate until a predetermined change in torque is detected in the output drives using one or more torque sensors and rotary encoders. A reduction in torque may indicate that the input drives of the surgical tool encountered resistance and have physically engaged with their corresponding output drives of the tool driver.

In some variations, one or more of the tool driver, sterile adapter, and surgical tool may output a fifth light pattern to indicate the tool readiness state (210). In some variations, one or more of the tool driver, sterile adapter, and surgical tool may output solid colored light (e.g., green light) at a predetermined light intensity using an optical waveguide of one or more of the tool driver, sterile adapter, and surgical tool. Additionally or alternatively, a display device may display a message to the operator such as "Tool ready for use" and/or "Tool fully attached." In some variations, an audio device may output one or more extended bings (longer than a short bing) at a predetermined frequency (different from the third audio pattern) and volume for a predetermined length of time. A fifth haptic pattern may inhibit haptic output. In other variations, the audio device may output the message displayed by the user console and/or verbally describe the actuation of the tool driver in response to the tool readiness state (210). In some variations, an electronic communication device (e.g., wireless communication device) of the surgical tool may transmit tool functionality and other data (e.g., security data, usage data, log data, diagnostic data, manufacturing data, etc.) to the electronic communication device of the tool driver. In turn, the electronic communication device of the surgical tool may receive authentication data and/or other data (calibration data, usage data, surgical system data, patient data, procedure data, regulatory data, etc.) that may be stored in a memory of the surgical tool. In some variations, the tool driver may be configured to wirelessly transfer power from the tool driver to the surgical tool in the surgical tool readiness state using a near-field wireless power transfer system.

Surgical Tool Release State

The methods described here may also control a tool driver in response to operator release of a surgical tool and/or sterile adapter from a tool driver. Generally, the operator may detach one or more of the surgical tool and sterile adapter from the tool driver through partial detachment (e.g., by actuating a surgical tool release mechanism) or full detachment (e.g., physical removal by lifting and/or pulling) of the surgical tool and/or sterile adapter from the tool driver. Partial detachment may be analogous to partial attachment. For example, the operator may detach the sterile adapter (having the surgical tool partially or fully attached thereon) from the tool driver (232) to transition from either the tool engagement state (208) or tool readiness state (210) to the surgical tool release state (212). The sterile adapter in the surgical tool release state (212) may be partially detached so as to lie on the tool driver but not output torque communicated by the tool driver. The operator is then able to wholly remove the surgical tool and sterile adapter from the tool driver to transition from the surgical tool release state (212) to the surgical tool removed state (214).

As shown in FIG. 2, the surgical tool that is partially attached (e.g., in the tool engagement state (208)) may transition to the surgical tool release state (212) either through partial detachment of the sterile adapter from the tool driver (232) or partial detachment of the surgical tool from the sterile adapter (234). For example, when an operator detaches the surgical tool from the surgical system (e.g., for tool switching), the operator may actuate a tool release mechanism (not shown) on the surgical tool to bias a portion of the surgical tool away from the sterile adapter. That is, an actuation mechanism (e.g., lever, button) of the surgical tool may release and/or partially separate the surgical tool from of the sterile adapter. This corresponds to transition from either the tool engagement state (208) or tool readiness state (210) to a surgical tool release state (212). In some variations, transition from either the tool engagement state (208) or the tool readiness state (210) to the tool release state (212) may correspond to generation of a sensor signal from one or more surgical tool sensors corresponding to detachment between the surgical tool and the sterile adapter (234). For example, one or more projections (e.g., biasing pegs) of the tool driver may generate a sensor signal corresponding to at least one projection being biased toward a surface of the tool driver (e.g., the sterile adapter partially exerting a downward force against the tool driver) when being detached.

In some variations, a second surgical tool sensor (e.g., proximity sensor, magnetic field transducer, Hall effect sensor) disposed on a distal end of the tool driver may generate a sensor signal corresponding to the presence of the surgical tool. This signal may indicate that the surgical tool is at least in partial contact with the sterile adapter. A sterile adapter sensor may generate a sensor signal corresponding to attachment between the tool driver and the sterile adapter. The combination of these surgical tool and sterile adapter sensor signals may be used by the controller to transition the system to the surgical tool release state (212). In some variations, the electronic communication devices of the tool driver and surgical tool may communicate and/or transfer power with each other as they are still within close proximity to each other.

In some variations, the sterile adapter may be partially detached from the tool driver by lifting up and separating (e.g., unlocking) a distal end of the sterile adapter from the tool driver. For example, transition from the tool engagement state (208) or the tool readiness state (210) to the tool release state (212) may correspond to generation of a sensor signal from a sterile adaptor sensor corresponding to detachment between the sterile adapter and the tool driver (232). In this state, the surgical tool may still be fully or partially attached to the sterile adapter. Likewise, one or more surgical tool sensors may output a sensor signal corresponding to detachment between the surgical tool and the tool driver. In response, the tool driver may be inhibited from driving an output drive. This combination of sensor signals may comprise partial detachment. For example, the sterile adapter may lie on the tool driver but be functionally decoupled from the tool driver. In response to the tool release state (212), a controller may inhibit actuation of the rotatable output drives of the tool driver.

In some variations, the tool driver may output a sixth light pattern in response to the partial detachment state. In some variations, one or more of the tool driver and sterile adapter may output a fast pulse of colored light (e.g., red light) at a predetermined light intensity using one or more optical waveguides of the tool driver and sterile adapter. For example, the sixth light pattern may comprise pulses of light having a duration of less than about half a second (e.g., about ¼ second). In some variations, detachment of the surgical tool from the sterile adapter may mechanically decouple the third optical waveguide of the surgical tool from the second optical waveguide of the sterile adapter such that light generated by the tool driver may be distributed to and output only by the first optical waveguide of the tool driver and/or second optical waveguide of the sterile adapter. This may allow an operator to quickly confirm the tool release state (212) based on which system component is emitting light.

Additionally or alternatively, a display device may output text or an image indicating that the surgical tool is partially detached from the sterile adapter or tool driver in the tool release state (212). For example, a user console coupled to the system may display a message to the operator such as "Surgical tool disengaged, please remove the surgical tool," "Sterile adapter disengaged, please remove the sterile adapter," and/or "Do you wish to remove the surgical tool?" In some variations, an audio device may output a sixth audio pattern corresponding to the tool release state (212). For example, the audio device may output a set of fast, short bings at a predetermined frequency (different from the frequency of the second and fourth audio pattern) and volume for a predetermined length of time. A haptic device may output a sixth haptic pattern corresponding to the tool engagement state (208). For example, a haptic device of the tool driver may output a small vibration. In other variations, the audio device may output the message displayed by the user console and/or verbally describe tool driver response to operator detachment.

Surgical Tool Removed State

An operator may fully detach the surgical tool and/or sterile adapter from the tool driver. In response, a controller may determine that the system transitions from the surgical tool release state (212) to the surgical tool removed state (214) corresponding to complete detachment of the surgical tool from the tool driver (236). Transition from the tool release state (212) to the tool removed state (214) may be based on generation of a sensor signal from one or more surgical tool sensors corresponding to detachment of the surgical tool from the tool driver (236). For example, one or more biased projections of the tool driver may generate a sensor signal corresponding to the surgical tool being withdrawn from contact with the projections of the tool driver. Furthermore, a second surgical tool sensor disposed on a distal end of the tool driver may output a sensor signal corresponding to the absence of the surgical tool when a magnetic projection of the surgical tool is not detected. The combination of these surgical tool sensor signals may be used by the controller to transition the system to the tool removed state (214). In some variations, electronic communication devices of the tool driver and surgical tool may move out of range of each other in the removed state (214).

In response to the surgical tool removed state (214), the controller may inhibit actuation of the rotatable output drives of the tool driver. In some variations, the tool driver may output a seventh light pattern in response to tool removal. In some variations, one or more of the tool driver and sterile adapter may output solid colored light (e.g., blue light) at a predetermined light intensity using respective optical waveguides of the tool driver and/or sterile adapter.

Additionally or alternatively, a display device may output text or an image indicating that the surgical tool is removed from the tool driver in the tool removed state (214). For example, a user console coupled to the system may display a message to the operator such as "Surgical tool removed" and/or "Please attach a surgical tool." In some variations, audio and haptic output may be inhibited in the tool removed state (214). In other variations, the audio device may output the message displayed by the user console and/or verbally describe the tool driver response to operator detachment.

Once a surgical tool is removed, the operator may either attach another surgical tool and/or sterile adapter to the tool driver. For example, the controller may transition the system from the tool removed state (214) to the sterile adapter ready state (202) when a sensor signal generated by a sterile adaptor sensor corresponds to detachment between the sterile adapter and the tool driver (238). The tool driver may be inhibited from driving an output drive in the sterile adapter detachment state (238). In some variations, one or more of visual, audio, and haptic output may also be inhibited when the sterile adapter is detached (238).

In some variations, the controller may transition from a tool removed state (214) to a tool loading readiness state (206). Transition from the tool removed state (214) to the tool loading readiness state (206) may be triggered by a sensor signal generated by a sterile adaptor sensor corresponding to full attachment between the sterile adapter and the tool driver (240). In response to sterile adapter attachment (240), a controller may inhibit actuation of the rotatable output drives of the tool driver. In some variations, the tool driver may output a third light pattern in response to the sterile adapter attachment state (240). For example, the tool driver may output solid colored light (e.g., blue light) at a predetermined light intensity using an optical waveguide of the tool driver and/or sterile adapter.

Additionally or alternatively, a display device may output text or an image indicating that the system is ready for attachment of a surgical tool to the sterile adapter and tool driver. For example, a user console coupled to the system may display a message to the operator such as "Please attach a surgical tool to the tool driver" and/or "Ready for tool loading." In some variations, an audio device may output the third audio pattern corresponding to the tool loading readiness state (206) as described herein. Haptic output may be inhibited as in the third haptic pattern.

In some variations, control of the tool driver may be based on attachment state and time. For example, if partial attachment of one or more of a sterile adapter and surgical tool to a tool driver does not transition to full attachment within a predetermined period of time and/or a predetermined number of attempts, then a controller may inhibit tool driver output and notify the operator of the attachment error. In response, the operator may repeat the attachment process.

II. Devices

A robotic surgical system may include one or more of the components necessary to perform robotic surgery using the devices as described herein. Generally, the devices described herein for use in a robotic surgical system may include one or more of a tool driver, a sterile adapter, and a surgical tool. The tool driver may include at least one rotatable output drive configured to communicate torque to the surgical tool through the sterile adapter. The sterile adapter may include a frame configured to be interposed between the tool driver and the surgical tool. A plate assembly may be coupled to the frame and at least one rotatable coupler may be supported by the plate assembly and configured to communicate the torque from the output drive of the tool driver to the surgical tool. The surgical tool may include at least one input drive configured to receive the torque communicated from the tool driver. The surgical tool may further include an end effector operatively coupled to the input drive.

In some variations, the tool driver may include an illumination source configured to emit light and an optical waveguide configured to propagate the emitted light to a sterile adapter. The sterile adapter and surgical tool may include respective optical waveguides configured to receive, propagate, and distribute the received light. In some variations, the tool driver may include at least one sterile adapter sensor and surgical tool sensor configured to generate a sensor signal used in turn to generate attachment data. The tool driver and surgical may each further comprise an electronic device configured for wireless communication and/or wireless power transfer. The electronic devices may be disposed in respective housings such that the electronic devices are in close proximity to each other when the tool driver, sterile adapter, and surgical tool are attached to each other.

Optical Waveguide

The tool driver, sterile adapter, and surgical tool as described herein may include one or more output devices configured to communicate information to an operator such as an attachment state, system or device state, and other information (e.g., patient data, procedure data, etc.). Information may be communicated visually by one or more of the tool driver, sterile adapter, and surgical tool and provide an intuitive indication of the attachment state of the surgical system to aid in efficient tool switching and sterile barrier formation. For example, one or more of the tool driver, sterile adapter, and surgical tool may include an optical waveguide (e.g., light pipe, light distribution guide, etc.) for allowing the operator to visualize attachment state information generated by the system. One or more optical waveguides may receive light from a light source (e.g., illumination source of a tool driver) using a predetermined combination of light output parameters (e.g., wavelength, frequency, intensity, pattern, duration) to confirm a formation state of the sterile barrier and/or robotic surgical system.

In some variations, an optical waveguide may be configured to receive and propagate light from an illumination source upon mechanical attachment to another optical waveguide of the robotic surgical system such that they are in optical communication. For example, a tool driver optical waveguide may be configured to output light to an input of a sterile adapter optical waveguide upon attachment to the tool driver. That is, light emitted and propagated by the tool driver may be received by the sterile adapter only after the sterile adapter is properly attached to the tool driver. This allows an operator to easily confirm an attachment state based on light output from the set of optical waveguides. The optical waveguides may be formed integral with the housings of the system to simplify manufacturing and allowing for a compact design and minimal power usage. Additionally or alternatively, the system may include a user console having additional visual output devices (e.g., display device). In some variations, the operator may receive audio and haptic feedback, as described herein, corresponding to the attachment state of the system.

A. Tool Driver

FIG. 3A is a perspective view of a tool driver (310) comprising a first optical waveguide (320) for communicating to a user (e.g., an operator) an attachment state of the system using outputted light. As shown in the variation depicted in FIG. 3A, the tool driver (310) may comprise a first housing (312), a set of surgical tool sensors (314), and a set of rotatable output drives (316). The set of output drives (316) may be supported by the first housing (312) and may be configured to communicate torque to a surgical tool through a sterile adapter (shown in FIGS. 3B and 3C). The tool driver (310) may be coupled to, for example, a distal end of a robotic arm (not shown). The first housing (312) may comprise a first optical waveguide (320). An optical waveguide may refer to a physical structure that guides electromagnetic waves such as visible light spectrum waves to passively propagate and distribute received electromagnetic waves. Non-limiting examples of optical waveguides include optical fiber, rectangular waveguides, light tubes, light pipes, combinations thereof, or the like. For example, light pipes may comprise hollow structures with a reflective lining or transparent solids configured to propagate light through total internal reflection. The optical waveguides described herein may be made of any suitable material or combination of materials. For example, in some variations, the optical waveguide may be made from optical-grade polycarbonate. In some variations, the housings and frames as described herein may be co-injected molded to form the optical waveguides. In other variations, the optical waveguides may be formed separately and coupled to a respective housing or frame.

As shown in FIG. 3A, the first optical waveguide (320) may be disposed along an exterior surface of the first housing (312). For example, the first optical waveguide (320) may be flush with an exterior surface of the first housing (312). In another example, the first optical waveguide (320) may be at least partially recessed or at least partially projected from the exterior surface of the first housing (312). In some variations, the first optical waveguide (320) may comprise a plurality of portions (e.g., disposed on opposite sides of the tool driver (310)). For example, as shown in FIG. 3A, the first optical waveguide (320) may include a strip located at least in part on a proximal end of the first housing (312). The strip may include a first end extending at least partially onto a first side (e.g., left side) of the first housing (312) and a second end extending at least partially onto a second side (e.g., right side) of the first housing (312). As another example, the first optical waveguide (320) may cover a substantial portion of the exterior of the first housing (312) (e.g., a proximal portion, side portions).

In some variations, the optical waveguides described herein may comprise one or more portions configured to emit light. For example, at least one of the portions may comprise one or more shapes including, for example, a circle, triangle, rectangle, diamond, polygon, symbol (e.g., plus/minus sign, arrow, lock, etc.), combinations thereof, or the like. For example, the first optical waveguide (320) may comprise three circles on each of the first and second sides of the first housing (312). The circles may be coupled to corresponding illumination sources, as described in detail herein, and configured to output light corresponding to a respective status of a tool driver, sterile adapter, and surgical tool. For example, a first circle may pulse blue light while a second and third circle may emit a solid red light when the tool driver is operational and in a sterile adapter ready state (202). These light patterns may correspond to the tool driver in a ready state and the sterile adapter and surgical tool unattached to the tool driver. In some variations, the first optical waveguide (320) may be located on the first housing (312) so as to be easily viewed simultaneously from multiple vantage points.

In some variations, the optical waveguides described herein may comprise a surface texture including, for example, a multi-faceted surface configured to increase visibility from predetermined vantage points. For example, the first optical waveguide (320) may comprise a convex shape.

The housing (312) may further comprise one or more illumination sources (not shown) coupled to the first optical waveguide (320). For example, the illumination source may be disposed at one or more of a left side, right side, proximal end, and distal end of the housing. The illumination source may be coupled to a power source through a robotic arm and configured to emit light using a predetermined combination of light output parameters (e.g., wavelength, frequency, intensity, pattern, duration, etc.). For example, the illumination source may be controlled by a controller to emit a plurality of light patterns having different colors corresponding to different attachment states, as described herein. In some variations, a characteristic of the light (e.g., color, pattern, etc.) may correspond to an attachment state between at least two of the tool driver, the sterile adapter, and the surgical tool, as described for example with respect to FIG. 2. Non-limiting examples of an illumination source include incandescent, electric discharge (e.g., excimer lamp, fluorescent lamp, electrical gas-discharge lamp, plasma lamp, etc.), electroluminescence (e.g., light-emitting diodes, organic light-emitting diodes, laser, etc.), induction lighting, and fiber optics. In FIG. 3A, the illumination source may be disposed within the first housing (312) but in some variations may be disposed external to the first housing (312). In some variations, the illumination source may be disposed within a proximal end of the first housing (312).

The first optical waveguide (320) may be configured to receive the light emitted by the illumination source (e.g., as a bezel or other suitable structure located over the illumination source). In some variations, the first optical waveguide (320) may be configured to emit a predetermined percentage of light received from the illumination source and propagate the remaining percentage of light to a second optical waveguide (340) of a sterile adapter (330) (shown in FIG. 3B). For example, the first optical waveguide (320) may be configured to emit between about 10% and about 100% of light received from the illumination source. In some variations, the first optical waveguide (320) may be configured to emit about 33% of received light, and the second optical waveguide (340) may be configured to receive about 66% of the light emitted from the illumination source. In some other variations, the first optical waveguide (320) may be configured to emit about 50% of received light, and the second optical waveguide (340) may be configured to receive about 50% of the light emitted from the illumination source.

In some variations, the first optical waveguide (320) may comprise one or more outputs configured to physically mate with corresponding inputs of the second optical waveguide (340) so as enable light transmission between the first and second optical waveguides (320, 340). For example, mating between an output of the first optical waveguide (320) and a corresponding input of the second optical waveguide (340) may be facilitated with complementary and corresponding features (e.g., latch, interlocking tabs, tab-and-slot alignment features, mateable ridge and groove interfaces, and/or other suitable mating features, etc.). In some variations, one or more outputs of the first optical waveguide (320) may physically mate with corresponding inputs of the second optical waveguide (340) only when the tool driver and the sterile adapter are properly (e.g., fully and operationally) engaged or attached to one another. For example, if the sterile adapter is only partially engaged or attached to the tool driver, the first and second optical waveguides (320, 340) may be misaligned, thereby reducing and/or preventing light propagation from the first optical waveguide (320) to the second optical waveguide (340), thereby providing a visual indicator to the operator that the sterile adapter (330) is not properly attached to the tool driver (310).

When the sterile adapter (330) is attached to the tool driver (310), light emitted from an illumination source of the tool driver (310) may be propagated through the first and second optical waveguides (320, 340), as described in further detail below. In some variations, the first optical waveguide (320) may emit substantially all the light received from the illumination source.

B. Sterile Adapter

FIG. 3B is a perspective view of a sterile adapter (330) coupled to the tool driver (310). In some variations, the sterile adapter (330) may comprise a second optical waveguide (340) for communicating an attachment state of the system (e.g., sterile adapter) using outputted light to a user such as an operator. As shown in FIG. 3B, the sterile adapter (330) may comprise a frame (332), a plate assembly (334) coupled to the frame (332), and at least one rotatable coupler (336) supported by the plate assembly (334). The plate assembly (334) may be configured to move up and down relative to the frame (332) within a predetermined range of motion, and the rotatable couplers (336) may be similarly configured to rotate and move up and down relative to the plate assembly (334). The sterile adapter (330) may be placed over the surgical tool sensors (314) and output drives (316). For example, when the sterile adapter (330) is attached to the tool driver (310) and surgical tool (350) (as shown in FIG. 3C), the frame (332) may be configured to be interposed between the tool driver (310) and the surgical tool (350). The rotatable couplers (336) may be configured to communicate torque generated by the output drive (316) of the tool driver (310) to the surgical tool (350).

The frame (332) may comprise a second optical waveguide (340). As shown in FIG. 3B, the second optical waveguide (340) may be disposed along an exterior surface of the frame (332) (e.g., along a lengthwise side portion of the sterile adapter (330), around at least a portion of the perimeter of the frame (332), etc.). For example, the second optical waveguide (340) may include a strip extending at least partially onto a first side (e.g., left side) of the frame (332) and at least partially onto a second side (e.g., right side) of the frame (332). The strip may further extend at least partially onto a distal side of the frame (332) so as to couple the first and second sides of the second optical waveguide (340). As depicted, the second optical waveguide (340) may be flush with the frame (332). In some variations, the second optical waveguide (340) may be located on the frame (332) so as to be easily viewed simultaneously from multiple vantage points.

The second optical waveguide (340) may be configured to receive light emitted from an output of the first optical waveguide (320). For example, the second optical waveguide (340) may be configured to receive light emitted from the tool driver (310) upon attachment of the sterile adapter (330) to the tool driver (310), such that the second optical waveguide (340) distributes light (e.g., becomes illuminated) via light emitted from the tool driver (310) and propagated by the first optical waveguide (320) to the second optical waveguide (340). In some variations, the second optical waveguide (340) may be configured to emit a predetermined percentage of light received from the first optical waveguide (320) and propagate the remaining percentage of light to a third optical waveguide (360) of a surgical tool (350) (shown in FIG. 3C). In some variations, the second optical waveguide (340) may be configured to emit about 33% of the light emitted from the illumination source, and the third optical waveguide (360) may be configured to emit about 33% of the light emitted from the illumination source. In some other variations, the second optical waveguide (340) may be configured to emit about 50% of the light emitted from the illumination source.

In some variations, the second optical waveguide (340) may comprise one or more outputs configured to physically mate with corresponding inputs of a third optical waveguide (360) (e.g., in a manner similar to mating between the first and second optical waveguides, as described herein). For example, mating between an output of the second optical waveguide (340) and a corresponding input of the third optical waveguide (360) may be facilitated with complementary and corresponding features (e.g., interlocking tabs, tab-and-slot alignment features, mateable ridge and groove interfaces, and/or other suitable mating features, etc.). In some variations, one or more outputs of the second optical waveguide (340) may physically mate with corresponding inputs of the third optical waveguide (360) only when the sterile adapter and surgical tool are properly (e.g., fully and operationally) engaged or attached to one another. For example, if the surgical tool (350) is only partially engaged or attached to the sterile adapter (330), the second and third optical waveguides (340, 360) may be misaligned, thereby preventing light propagation from the second optical waveguide (340) to the third optical waveguide (360), thereby providing a visual indicator that the surgical tool (350) is not properly attached to the sterile adapter (330).

When the surgical tool (350) is attached to the sterile adapter (330) and the sterile adapter (330) is attached to the tool driver (310), light emitted from an illumination source of the tool driver (310) may be propagated through the first, second, and third optical waveguides (320, 340, 360). In some variations, the second optical waveguide (340) may emit substantially all the light received from the first optical waveguide (320).

In some variations, the sterile adapter (330) may comprise a second illumination source (not shown) such that the second optical waveguide (340) may be configured to receive the light emitted by the second illumination source. In some of these variations, the second optical waveguide (340) may receive light only from the second illumination source and not the first illumination source of the tool driver (310). In some variations, the second illumination source may be battery powered. In some variations, the second optical waveguide (340) may be configured to emit a predetermined percentage of light received from the second illumination source and propagate the remaining percentage of light to the third optical waveguide (360). For example, the second optical waveguide (340) may be configured to emit between about 10% and about 100% of light received from the second illumination source. In some other variations, the second optical waveguide (340) may be configured to emit about 50% of received light, and the third optical waveguide (360) may be configured to receive about 50% of the light emitted from the second illumination source. In some variations, the second optical waveguide (340) and second illumination source may be configured to propagate light to the first and third optical waveguides (320, 360). In some of these variations, the second optical waveguide (320) may be configured to emit about 33% of received light, and the first and third optical waveguides (320, 360) may be configured to each emit about 33% of the light emitted from the second illumination source.

In some variations, the sterile adapter (330) may comprise a switch configured to activate the second illumination source upon physical attachment of the second optical waveguide (340) to at least a portion of the tool driver (e.g., a distal end of the tool driver, first optical waveguide, etc.). The switch may be, for example, a conductive contact switch, mechanical contact switch (e.g., slide switch), and the like. Accordingly, the second optical waveguide (340) may emit light received from the second illumination source only when the tool driver (310) and the sterile adapter (330) are properly (e.g., fully and operationally) attached engaged or attached to each other and the switch is activated.

C. Surgical Tool

FIG. 3C is a perspective view of a surgical tool (350) coupled to the sterile adapter (330) and tool driver (310). In some variations, the surgical tool (350) may comprise a third optical waveguide (360) for communicating an attachment state to an operator. As shown in FIG. 3C, the surgical tool (350) may comprise a second housing (352) configured to couple to the sterile adapter (330). The surgical tool (350) may comprise at least one input drive (not shown) supported by the second housing (352) and configured to receive the torque communicated from the output drive of the tool driver (310). The surgical tool (350) may further comprise an end effector (not shown) that may extend from the second housing (352) and be operatively coupled to at least one input drive.

The second housing (352) may comprise a third optical waveguide (360) configured to receive light from the second optical waveguide (340). As shown in FIG. 3C, the third optical waveguide (360) may be disposed along an exterior surface of the second housing (352) (e.g., extending widthwise and perpendicular to the second optical waveguide (340) of the sterile adapter (330)). For example, the third optical waveguide (360) may include a strip extending at least partially onto a first side (e.g., left side) of the second housing (352) and at least partially onto a second side (e.g., right side) of the second housing (352). The strip may further extend at least partially onto a third side (e.g., top side) of the second housing (352) so as to couple the first and second sides of the third optical waveguide (360).

The third optical waveguide (360) may be configured to receive light emitted from an output of the second optical waveguide (340) of the sterile adapter (330). For example, the third optical waveguide (360) may be configured to receive light emitted from the tool driver (310) upon attachment of the surgical tool (350) to the sterile adapter (330) when the sterile adapter (330) is attached to the tool driver (310), such that the third optical waveguide (360) distributes light (e.g., becomes illuminated) via light emitted from the tool driver (310) and propagated by the first and second optical waveguides (320, 340) to the third optical waveguide (360). In other words, when the surgical tool (350) is attached to the sterile adapter (330) and the sterile adapter (330) is attached to the tool driver (310), light emitted from an illumination source of the tool driver (310) may be propagated through the first, second, and third optical waveguides (320, 340, 360). In some variations, the third optical waveguide (360) may emit substantially all the light received from the second optical waveguide (340).

In some variations, the surgical tool (350) may comprise a third illumination source (not shown) such that the third optical waveguide (360) may be configured to receive the light emitted by the third illumination source. In some of these variations, the third optical waveguide (360) may receive light only from the third illumination source and not the first and/or second illumination sources. In some variations, the third illumination source may be battery powered or wirelessly powered using an electronic device as described in detail with respect to FIG. 8. In some variations, the third optical waveguide (360) may emit substantially all the light emitted from the third illumination source. In some variations, the third optical waveguide (360) may be configured to emit a predetermined percentage of light received from the third illumination source and propagate the remaining percentage of light to the first and/or second optical waveguides (320, 340). For example, the third optical waveguide (360) may be configured to emit between about 10% and about 100% of light received from the third illumination source. In some other variations, the third optical waveguide (360) may be configured to emit about 50% of emitted light, and the second optical waveguide (340) may be configured to emit about 50% of the light emitted from the third illumination source. In some variations, the third optical waveguide (360) and third illumination source may be configured to propagate light to the second and/or first optical waveguides (340, 320). In some of these variations, the third optical waveguide (360) may be configured to emit about 33% of emitted light, and the first and second optical waveguides (320, 340) may be configured to each emit about 33% of the light emitted from the third illumination source.

In some variations, the surgical tool (350) may comprise a switch configured to activate the third illumination source upon physical attachment of the third optical waveguide (360) to at least a portion of the sterile adapter (e.g., a distal end of the sterile adapter, second optical waveguide, etc.). The switch may be, for example, a conductive contact switch, mechanical contact switch (e.g., slide switch), and the like. Accordingly, the third optical waveguide (360) may emit light received from the third illumination source only when the surgical tool (350) and the sterile adapter (330) are properly (e.g., fully and operationally) attached engaged or attached to each other and the switch is activated.

In some variations, the optical waveguides of the tool driver (310), sterile adapter (330), and surgical tool (350) may be disposed along different portions of the system to aid identification of the attached device component. For example, the first optical waveguide (320) may be disposed at an end of the tool driver (310), the second optical waveguide (340) may be disposed along a length of the sterile adapter (330), and the third optical waveguide (360) may be disposed perpendicular to the second optical waveguide (340) and across a top of the surgical tool (350). In other variations, three optical waveguides may disposed respectively at a distal end, intermediate portion, and proximal end.

Additionally or alternatively, one or more optical waveguides may be disposed along one or more of a robotic arm, display, surgical platform, or the like. For example, an optical waveguide disposed on one or more portions of a robotic arm may be configured to communicate an attachment state of the robotic arm to a tool driver. As another example, a surgical platform may comprise one or more optical waveguides disposed along a perimeter of a top surface of the platform and may be configured to communicate one or more of an operational state, attachment state, procedure state, or the like, of the robotic surgical system. Any of the optical waveguides as described herein may communicate a state of any of the components of the system.

Surgical Tool Sensors

The tool driver as described herein may include one or more surgical tool sensors configured to generate a sensor signal corresponding to an attachment state (e.g., partial attachment, full attachment, partial detachment, full detachment, improper attachment) between the tool driver and surgical tool. The surgical tool sensors described herein may be used to directly or indirectly determine a proximity of a surgical tool to the tool driver. The attachment state may be used to control the tool driver and/or notified to an operator. The surgical tool sensor may be, for example, a proximity sensor that may be used to determine a position of the surgical tool relative to the tool driver. For example, the surgical tool sensor may be disposed in one or more projections (e.g., cylindrical pegs) configured to bias away from a surface of the tool driver housing and toward a surgical tool. When a sterile adapter is coupled to the tool driver for attachment, the projections may be configured to contact the sterile adapter to urge a plate assembly upward and away from the tool driver. When a surgical tool is attached to the sterile adapter, the surgical tool will urge the plate assembly toward the tool driver and reduce projection height. By placing a surgical tool sensor within one or more of the projections, a sensor signal may be generated that corresponds to a change in height of the projection and an attachment state between the tool driver and surgical tool.

Figure 4A:
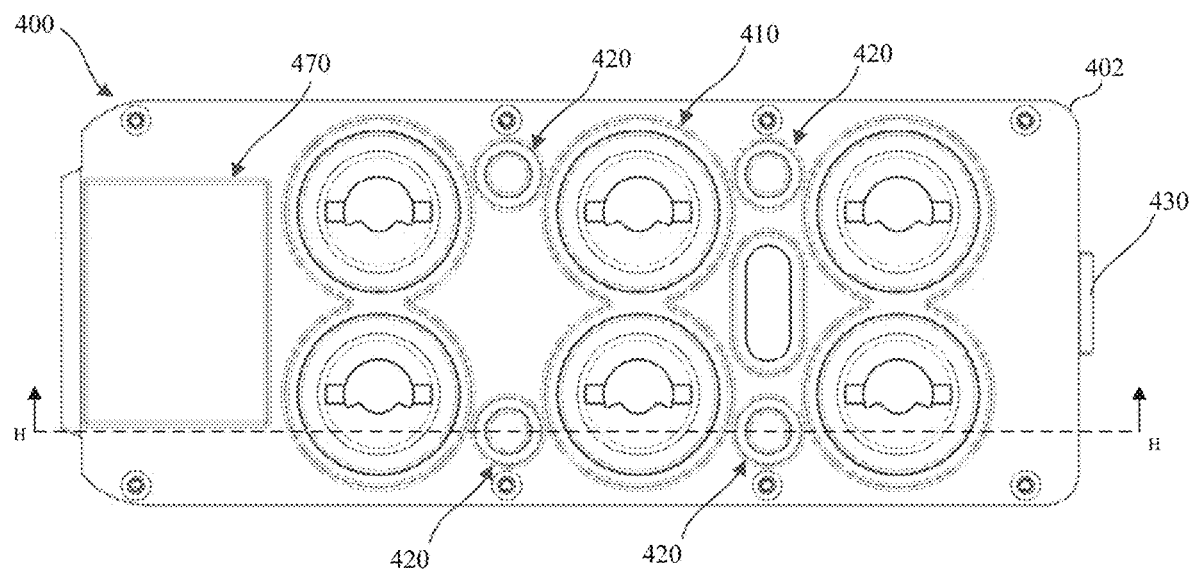
FIGS. 4A-4E are illustrative views of a variation of a tool driver in different configurations.
Figure 4B:
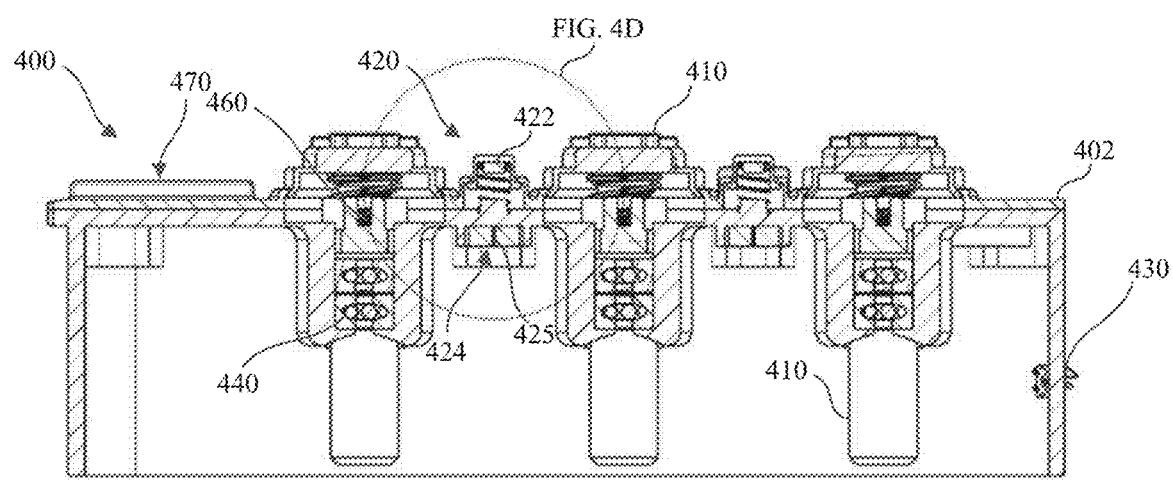
Figure 4C:
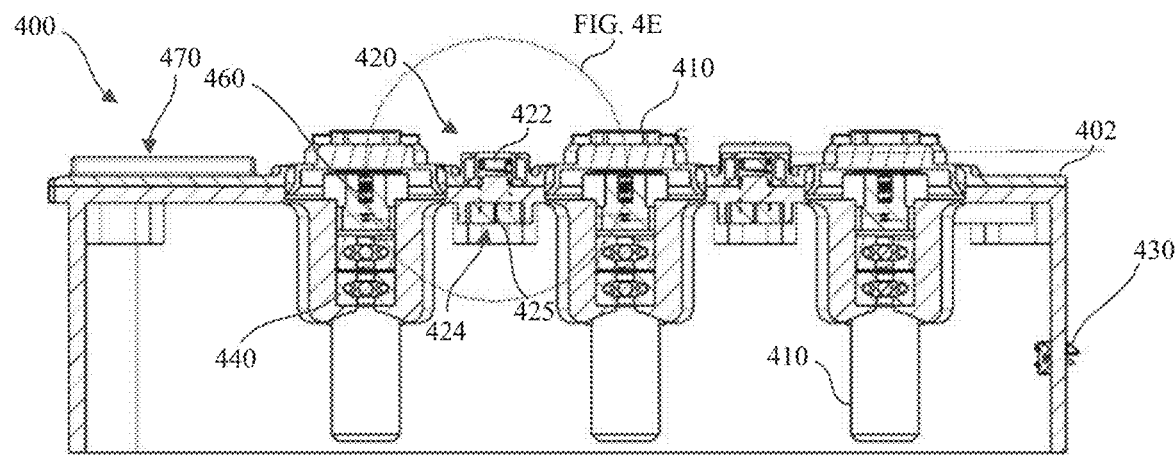

FIGS. 4A-4E are illustrative views of an exemplary variation of a tool driver (400) configured to attach to a surgical tool via a sterile adapter. FIG. 4A is a plan view of the tool driver (400). The tool driver (400) may comprise a first housing (402) configured to attach to a surgical tool via a sterile adapter. The tool driver (400) may comprise one or more rotatable output drives (410) supported by the first housing (402) where the output drives (410) may be configured to communicate torque to an input drive of the surgical tool through a sterile adapter. One or more of the output drives (410) may comprise one or more of a torque sensor (440) and rotary output encoder (460) configured to generate one or more sensor signals used to determine a change in torque of the output drive (410). In some variations, a sterile adapter sensor may comprise at least one of the torque sensor (440) and rotary output encoder (460) (FIGS. 4B and 4C). A change in torque may correspond to a change in engagement (e.g., attachment, detachment) between a rotatable coupler of a sterile adapter and the rotatable output drive (410) of the tool driver (400). FIG. 4A depicts six output drives (410) arranged on a surface of the first housing (402) in a bilaterally symmetric arrangement. Similarly, four projections (420) may be arranged in a bilaterally symmetric arrangement and may also be disposed between pairs of the output drives (410). This arrangement may aid detection of lateral and/or longitudinal misalignment of one or more of the sterile adapter and tool driver to the tool driver (400). Sensor signals from each of the projections (420) may be used together to generate attachment data. Although FIG. 4A depicts a tool driver with six rotary output drives (410) and four projections (420), it should be understood that in other variations, the tool driver may include fewer or more output drives (410) and/or projections (420). Additionally or alternatively, the tool driver (400) may include at least one linear output drive (e.g., a drive providing an axially-moving output), such as described in U.S. patent application Ser. No. 15/803,659, filed on Nov. 3, 2017 and entitled "TOOL DRIVER WITH LINEAR DRIVES FOR USE IN ROBOTIC SURGERY," which is incorporated herein in its entirety by reference.

Although some variations of the tool driver (400) may comprise a single projection (420) having a surgical tool sensor (424), a plurality of spaced apart first surgical tool sensors (424) may allow the system to determine an orientation of a plate assembly relative to the sterile adapter frame. That is, knowledge of an attachment state between the sterile adapter and tool driver (400) may be improved by using a plurality of first surgical tool sensors. For example, a surgical tool may be improperly attached to a sterile adapter and tool driver (400) when fewer than four projections (420) are pressed down to a predetermined height. If only three projections are urged downward with the fourth projection in a higher position, then the sensor signal output by the first surgical tool sensors (424) may correspond to an improper attachment state where the surgical tool is askew relative to the sterile adapter. In this position, one or more of the rotatable couplers (410) may be unable to communicate torque to the input drive of the surgical tool.

Figure 4D:
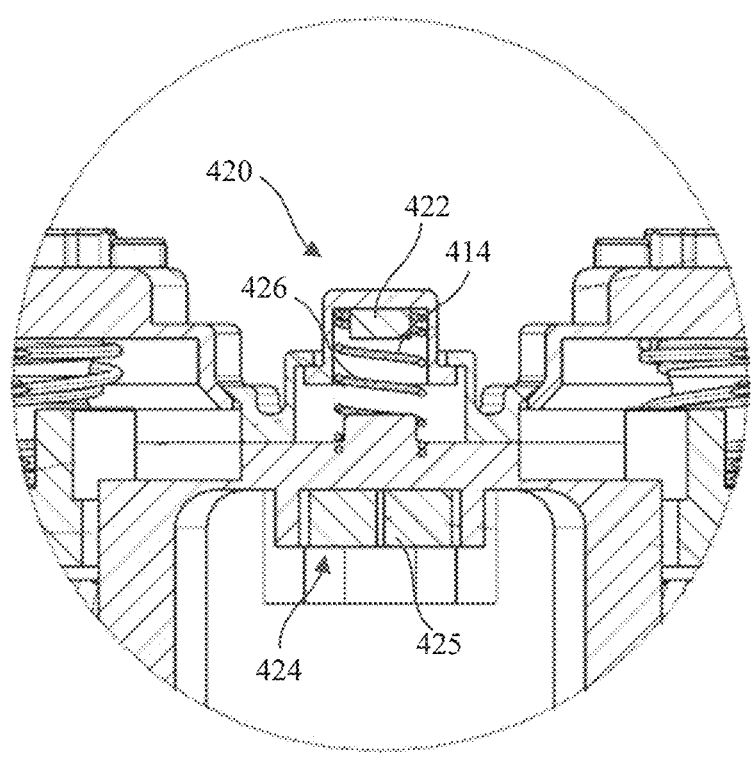
Figure 4E:
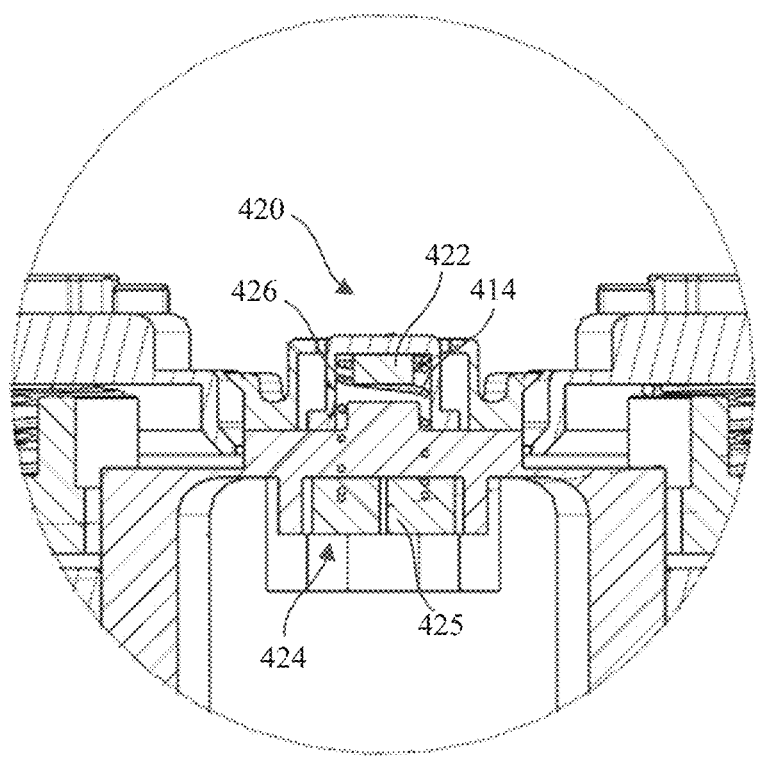

FIGS. 4B-4C are cross-sectional side views of the tool driver (400) along the H-H lines depicted in FIG. 4A. The tool driver (400) may comprise at least one rotatable output drive (410) supported by the first housing (402) and at least one projection (420) extending from a surface of the first housing (402) and configured to bias away from the surface, as shown in FIG. 4B. In some variations, the projection (420) may comprise a first surgical tool sensor (424) configured to generate a sensor signal comprising at least one attachment state between the tool driver (400) and the surgical tool. In some variations, the first surgical tool sensor (424) may be a proximity sensor configured to determine a proximity of first end of the projection (420) relative to the second end of the projection (420). As shown in FIGS. 4D and 4E, the proximity sensor may comprise a magnet (422) coupled to a first end of the projection (420) disposed on an exterior side of the first housing (402) and a magnetic field transducer (425) coupled to a second end of the projection (420) disposed on an interior side of the first housing (402). In some variations, the magnetic field transducer may be an analog sensor. In some variations, the projection (420) may comprise a complaint material (426) configured to bias the first end of the projection (420) away from the first housing (402). For example, the compliant material (426) may be a coil spring (414) (FIGS. 4D and 4E) coupled between the first end of the projection (420) and a surface of the first housing (402). In other variations, the projection (420) may comprise a leaf spring.

FIGS. 4A, 4B, and 4D illustrate the projections (420) in a first configuration where the projection (420) is fully biased away from a surface of the housing (402). For example, in the first configuration, the projection (420) is not in contact with either of the sterile adapter or the surgical tool. The first configuration of the projection (420) corresponds to, for example, a detachment state between the tool driver, sterile adapter, and surgical tool. FIGS. 4A, 4C, and 4E illustrate the projections (420) in a second configuration where the projection (420) is fully retracted toward the surface of the first housing (402) due to a compressive force such as from attachment of a surgical tool and sterile adapter (not shown). The second configuration of the projection (420) corresponds to, for example, an attachment state of the sterile adapter and/or surgical tool.

In some variations, an attachment state may correspond to a position of the projection (420) over time. For example, when the first surgical tool sensor (420) is in a first or second configuration for a predetermined amount of time, the sensor signal may correspond to either a detached state or attached state. A sterile adapter may be in a partial attachment state when the projection (420) transitions quickly from the first configuration to the second configuration and back to the first configuration. For example, an operator may attach a sterile adapter to a tool driver by rotating the sterile adaptor over the projections (420) to urge the projection toward the second configuration. Once the frame of the sterile adapter is latched into the tool driver, then the projections (420) may be biased toward the first configuration.

In some variations, a proximity sensor of a projection may comprise a Hall effect sensor. The magnet may be made of any suitable material or combination of materials. For example, in some variations, the magnet may be a permanent magnet, ferromagnetic magnetic, and paramagnetic magnet, and may be made from aluminum, platinum, iron, nickel, cobalt, copper, titanium, alloys or combinations thereof, or the like.

Figure 5A:
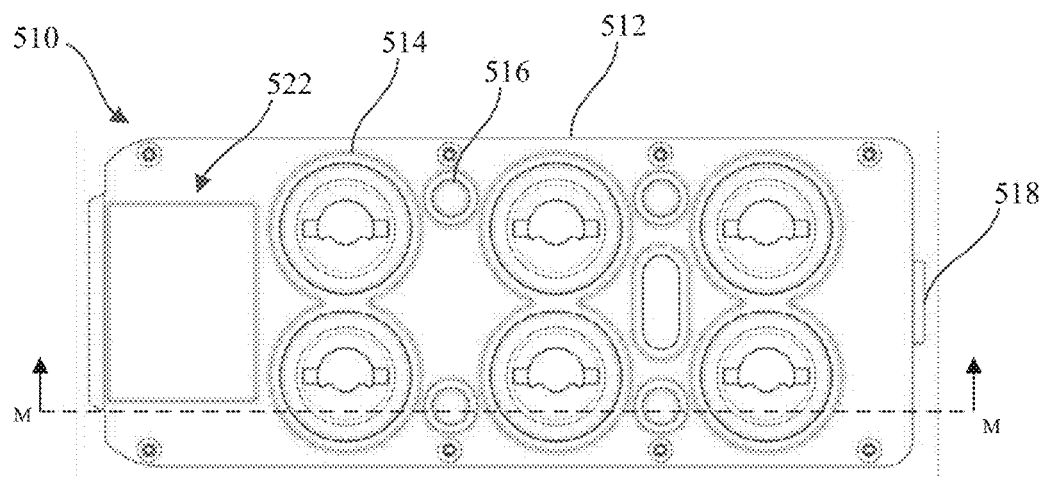
FIGS. 5A-5C are illustrative views of a variation of a tool driver and surgical tool.
Figure 5B:
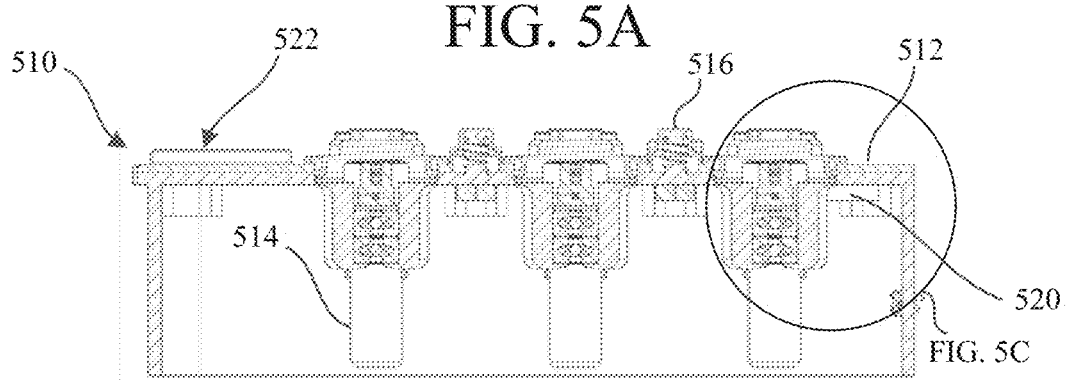

In some variations, a tool driver may comprise at least one second surgical tool sensor configured to directly sense a location of a surgical tool used for generating a sensor signal corresponding to an attachment state between the tool driver and surgical tool. FIG. 5A is a plan view of a tool driver (510) comprising a first housing (512), a set of output drives (514), and a set of projections (516) disposed on a surface of the first housing (512), a sterile adapter sensor (518) disposed on a distal end of the first housing (512), and a proximal end (522) of the first housing (512). In some variations, an electronic device (not shown) may be depicted within the proximal end (522). FIG. 5B is a cross-sectional side view of the tool driver (500) along the M-M line depicted in FIG. 5A. FIG. 5B depicts a second surgical tool sensor (520) disposed within a distal end of the first housing (512).

In some variations, an attachment state may correspond to a position of the projection (420) over time. For example, when the first surgical tool sensor (424) is in a first or second configuration for a predetermined amount of time, the sensor signal may correspond to either a detached state or attached state. A sterile adapter may be in a partial attachment state when the projection (420) transitions quickly from the first configuration to the second configuration and back to the first configuration. For example, an operator may attach a sterile adapter to a tool driver by rotating the sterile adaptor over the projections (420) to urge the projection toward the second configuration. Once the frame of the sterile adapter is latched into the tool driver, then the projections (420) may be biased toward the first configuration.

Figure 5C:
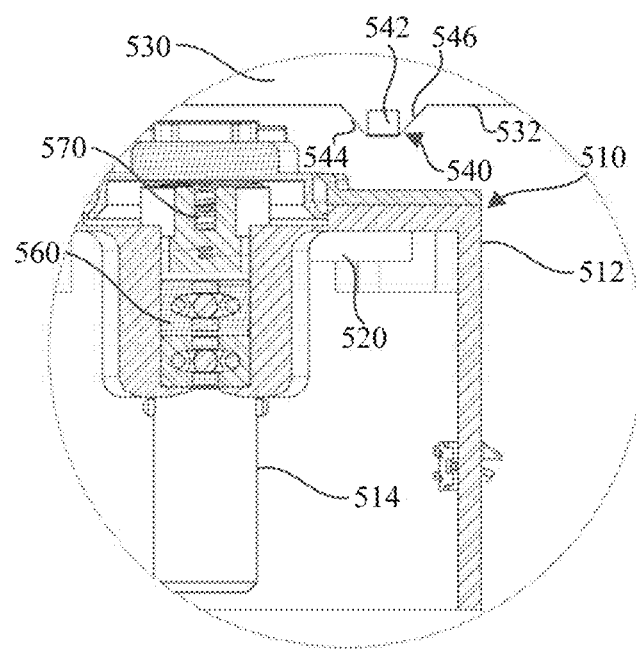

FIG. 5C is a detailed cross-sectional side view of the tool driver (510) depicted in FIG. 5B and shows a distal end of the surgical tool (530) within sensor range of the second surgical tool sensor (520). In FIG. 5C, a second surgical tool sensor (520) may be disposed within a distal end of the first housing (512) of the tool driver (510). In some variations, the second surgical tool sensor (520) may comprise a proximity sensor. For example, the proximity sensor may be a magnetic field transducer such as a Hall effect sensor. Opposite the second surgical tool sensor (520), a distal end of the surgical tool (530) may comprise a second housing (532) configured to attach to a sterile adapter (not shown for the sake of clarity). The second housing (532) of the surgical tool (530) may comprise a magnetic projection (542) configured to mate with a corresponding recess in a sterile adapter. The magnetic projection (542) may comprise a magnet as described herein. The magnetic projection (542) may comprise a first tapered surface (544) and a second tapered surface (546) opposite the first tapered surface (544).

A sterile adapter engagement feature (540) may comprise the distal end of the surgical tool (530) including the magnetic projection (542). The magnetic projection (542) may extend from a surface of the surgical tool (530) and be configured to slide over portions of the sterile adapter and be placed within a recess of the sterile adapter, as described in more detail with respect to FIGS. 6A and 6B. As discussed herein, the surgical tool (530) may comprise at least one input drive supported by a housing of the surgical tool (530) and may be configured to receive torque communicated from an output drive (514) of the tool driver (510) through the sterile adapter. For example, the tool drive may further include a torque sensor (560) and rotary output encoder (570). An end effector (not shown) may extend from the surgical tool housing and be operatively coupled to the input drive.

Figure 6A:
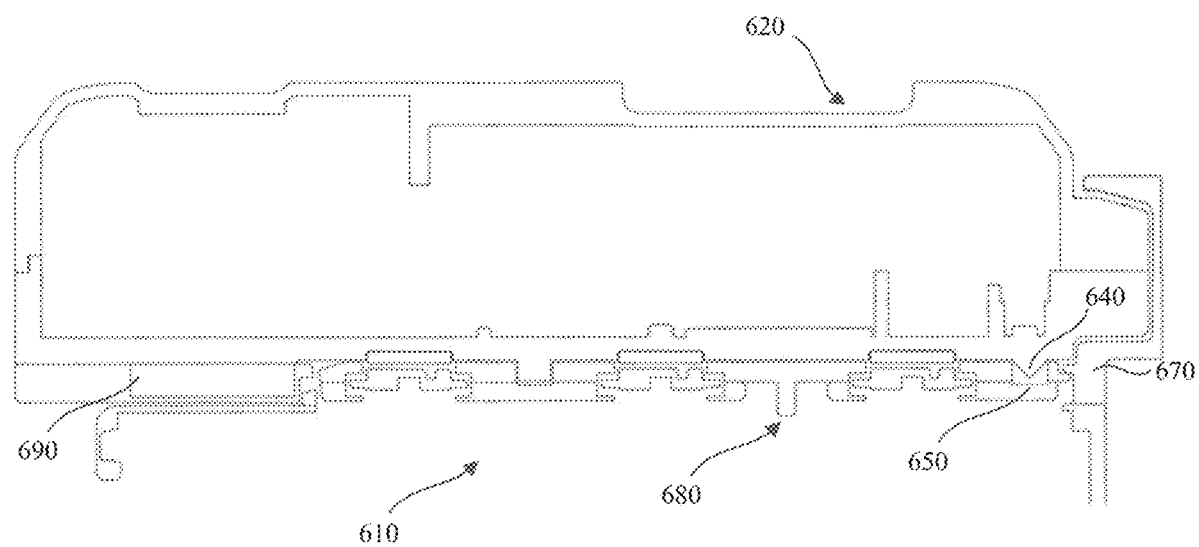
FIGS. 6A-6B are illustrative views of some variations of a sterile adapter and surgical tool.
Figure 6B:
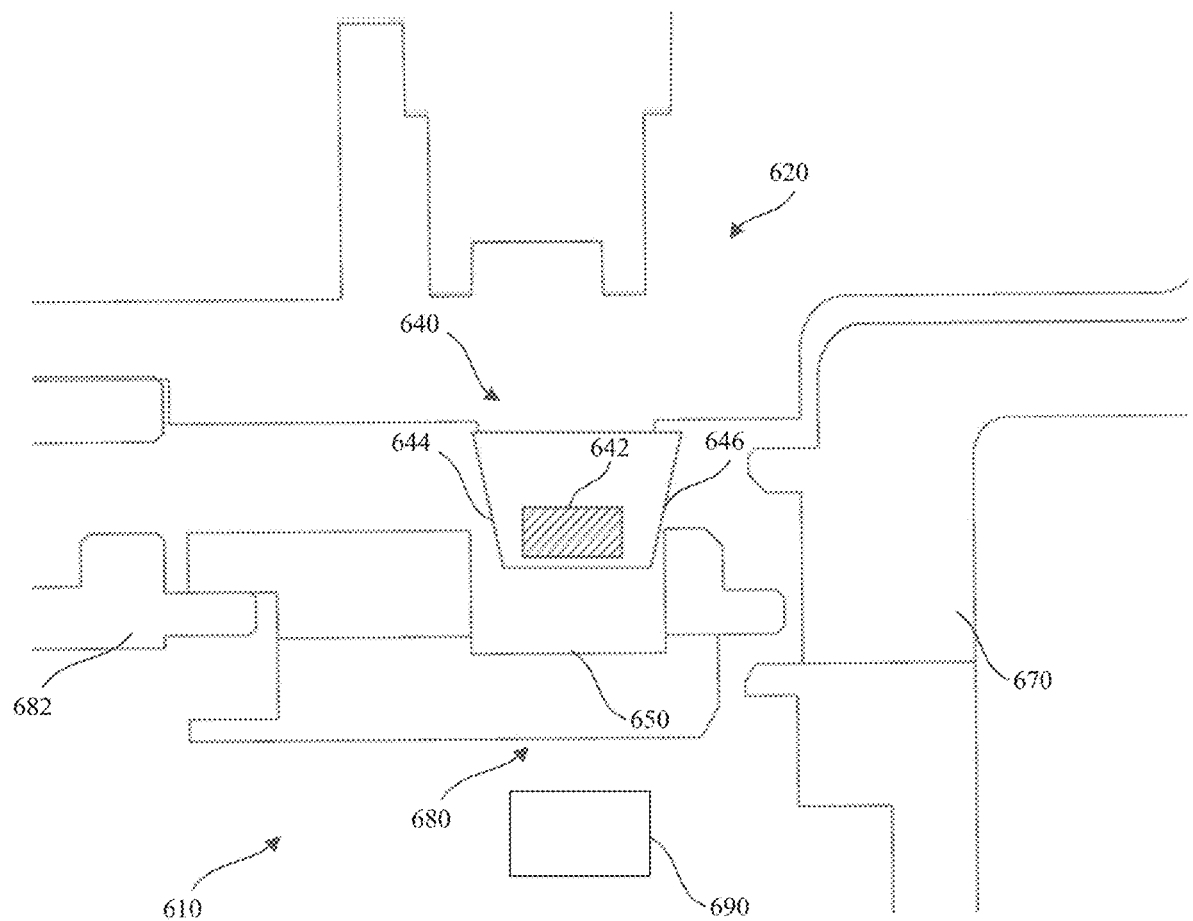

FIGS. 6A-6B are cross-sectional side views of a sterile adapter (610) and a surgical tool (620) comprising corresponding engagement features for mating the surgical tool (620) to the sterile adapter (610) in a desired orientation. For example, one or more engagement features may be configured to prevent an operator from attaching a distal end of the surgical tool to a proximal end of the sterile adapter. In some variations, a sterile adapter engagement feature (640) of the surgical tool (620) may comprise a magnetic projection (642) (see FIG. 6B) comprising a magnet as described herein and configured to be directly sensed by a second surgical tool sensor (690) of the tool driver. For example, the second surgical tool sensor (690) may comprise at least one of an inductive sensor, optical sensor, magnetic sensor, conductive contact switch, and/or mechanical contact switch. As depicted in FIG. 6A, a surgical tool (620) may comprise a sterile adapter engagement feature (640) that may protrude from a surface of the surgical tool (620) and be configured to engage with a surface of a sterile adapter (610). The sterile adapter engagement feature (640) and surgical tool engagement feature (650) may be disposed at respective distal ends of the surgical tool (620) and sterile adapter (610). The sterile adapter (610) may comprise a plate assembly (680) coupled to a frame (670), and a surgical tool engagement feature (650) disposed in the plate assembly (680) and configured to mate with the sterile adapter engagement feature (640). In some variations, a proximal end of the surgical tool (620) may comprise a projection configured to support an electronic communication device of the surgical tool (620), as discussed in more detail with respect to FIG. 8.

FIG. 6B is a detailed cross-sectional view of a distal end of the surgical tool (620) and sterile adapter (610). As discussed herein, the sterile adapter engagement feature (640) may project from a surface of the sterile adapter (620). In some of these variations, the sterile adapter engagement feature (640) may comprise a magnetic projection (642) comprising a first tapered surface (644) and a second tapered surface (646) opposite the first tapered surface (644). The tapered surfaces (644, 646) may be angled to allow the surgical tool (620) to slide over one or more portions of the sterile adapter (610) until the magnetic projection (642) mates with (e.g., slides into) the surgical tool engagement feature (650). For example, the sterile adapter engagement feature (640) may comprise a trapezoidal shape. The surgical tool engagement feature (650) may comprise a recess configured to hold the sterile adapter engagement feature (640) and limit movement of the surgical tool (620) relative to the sterile adapter (610). The recess may be distal to an output drive disc (682). A second surgical tool sensor (690) of a tool driver, as described herein, may overlap (e.g., disposed below) the surgical tool engagement feature (650). In some variations, the surgical tool (620) and sterile adapter (610) may comprise a plurality of spaced-apart engagement features. In some variations, the surgical tool engagement feature (640) may comprise a recess while the sterile adapter (650) may comprise a projection.

Sterile Adapter Sensor

In some variations, a tool driver may include at least one sterile adapter sensor configured to generate a sensor signal when the sterile adapter is fully attached to the tool driver. For example, the sterile adapter sensor may generate the sensor signal when the sterile adapter is physically latched onto a distal portion of the tool driver. The sensor signal may correspond to an attachment state (e.g., full attachment, full detachment) between the tool driver and sterile adapter. The tool driver and sterile adapter may each be configured so as to allow only one-way engagement between the sterile adapter and tool driver. That is, the distal end of the sterile adapter will not engage (e.g., latch into) with the tool driver unless the proximal ends of the sterile adapter and tool driver are mated to each other. The attachment state may be used to control the tool driver and/or notify an operator of the attachment state of the system. The sterile adapter sensor may be, for example, a switch sensor configured to generate a sensor signal upon physical contact with the sterile adapter.

In some variations, as shown in FIG. 4A, the first housing (402) may comprise a sterile adapter sensor (430) disposed at a distal end of the first housing (402). The sterile adapter sensor (430) may be configured to generate a sensor signal corresponding to an attachment state between the tool driver (400) and a sterile adaptor (not shown for clarity). Variations of a sterile adapter sensor are described in more detail herein with respect to FIGS. 7A-7C. In some variations, a proximal end (470) of the first housing (402) may be configured to support an electronic communication device of the tool driver (400), as described in more detail herein with respect to FIG. 8.

FIG. 7A is a plan view of a tool driver (710) coupled to a sterile adapter (720). The sterile adapter (720) may comprise a plate assembly (724) coupled to a frame (722). The frame (722) may be configured to be interposed between the tool driver (710) and surgical tool (not shown for clarity). A set of rotatable couplers (726) may be supported by the plate assembly (724) and configured to communicate torque from an output drive (714) of the tool driver (710) to the surgical tool.

Figure 7C:
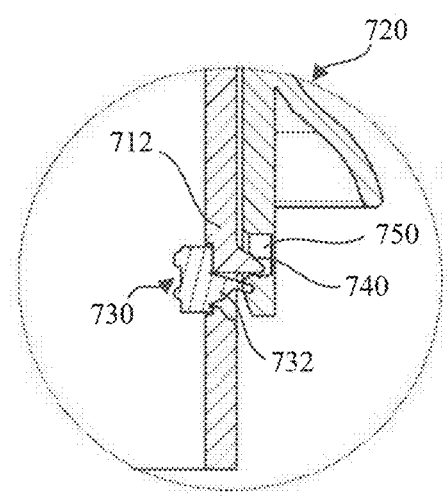

FIGS. 7B-7C are cross-sectional side views of the sterile adapter (720) and tool driver (710) along the K-K line in FIG. 7A. The tool driver (710) may comprise a housing (712) configured to couple to the sterile adapter (720). The housing (712) may comprise a sterile adapter engagement feature (740) mateable with a corresponding tool driver engagement feature (750) on the sterile adapter (720). A sterile adapter sensor (730) may be coupled to the sterile adapter engagement feature (740) and configured to generate a sensor signal when the tool driver engagement feature (750) is mated with its corresponding sterile adapter engagement feature (740). That is, the sterile adapter sensor (730) is disposed at a location that does not generate a sensor signal until the sterile adapter is securely attached to the tool driver. In some variations, the sterile adapter engagement feature (740) and sterile adapter sensor (730) may each be disposed on a distal end of the tool driver (710) on a side of a tool driver housing perpendicular to the rotatable output drive (714). As shown in FIG. 7C, the sterile adapter engagement feature (740) may comprise a projection, and the tool driver engagement feature (750) may comprise a recess. The projection may be configured (e.g., tapered) to allow the sterile adapter (720) to slide over the projection. The projection may then mate with the recess of the tool driver engagement feature (750). For example, the projection of the sterile adapter engagement feature (740) may comprise a tapered surface on one side and a flat surface opposite the tapered surface. The recess of the tool driver engagement feature (750) may be configured to limit movement of the sterile adapter (720) relative to the tool driver (710).

In some variations, a distal portion of the frame (722) projecting perpendicularly from a plane of the plate assembly (724) and comprising the tool driver engagement feature (750) may comprise a compliant material that may aid an operator in mating the sterile adapter to the tool driver using respective engagement features. In some variations, the tool driver (710) and sterile adapter (720) may comprise a plurality of spaced-apart engagement features. In some variations, the sterile adapter engagement feature (740) may comprise a recess while the tool driver engagement feature (740) may comprise a projection. Placing the sterile adapter engagement feature (740) and tool driver engagement feature (750) further away from the rotatable plate assembly (724) may help ensure that mating of the engagement features (740, 750) corresponds to proper attachment of the sterile adapter (720) to the tool driver (710). Accordingly, it is preferable for the engagement features (740, 750) to be the final portions of the sterile adapter (720) and tool driver (710) that couple to each other when the sterile adapter (720) is attached to the tool driver (720).

In some variations, the sterile adapter sensor (730) may comprise a proximity sensor configured to detect attachment between the sterile adapter engagement feature (740) and tool driver engagement feature (750). For example, the proximity sensor may comprise at least one of a conductive contact switch, mechanical contact switch (e.g., slide switch), Hall Effect sensor, forces sensor, optical sensor, combinations thereof, or the like. In FIG. 7C, the sterile adapter sensor (730) may comprise a switch (732) including a torsion spring configured to bias the switch (732) to an initial, reset position. In some variations, the switch (732) may be disposed adjacent to the sterile adapter engagement feature (740) such that the switch (732) is depressed when the engagement features (740, 750) mate.

Electronic Device

In some variations, at least one of the tool driver and surgical tool may include one or more electronic communication devices configured to transmit data to each other. Generally, a tool driver and surgical tool may include respective communication devices in close proximity to each other when the surgical tool is attached to the sterile adapter and tool driver. Communication performance may depend at least in part on placement of the communication devices within the tool driver and surgical tool. For example, minimizing the distance between the electronic communication devices may improve one or more of signal-to-noise ratio (SNR) and power efficiency. In some variations, the electronic devices may comprise a wireless power transfer system.

A. Tool Driver

Figure 8:
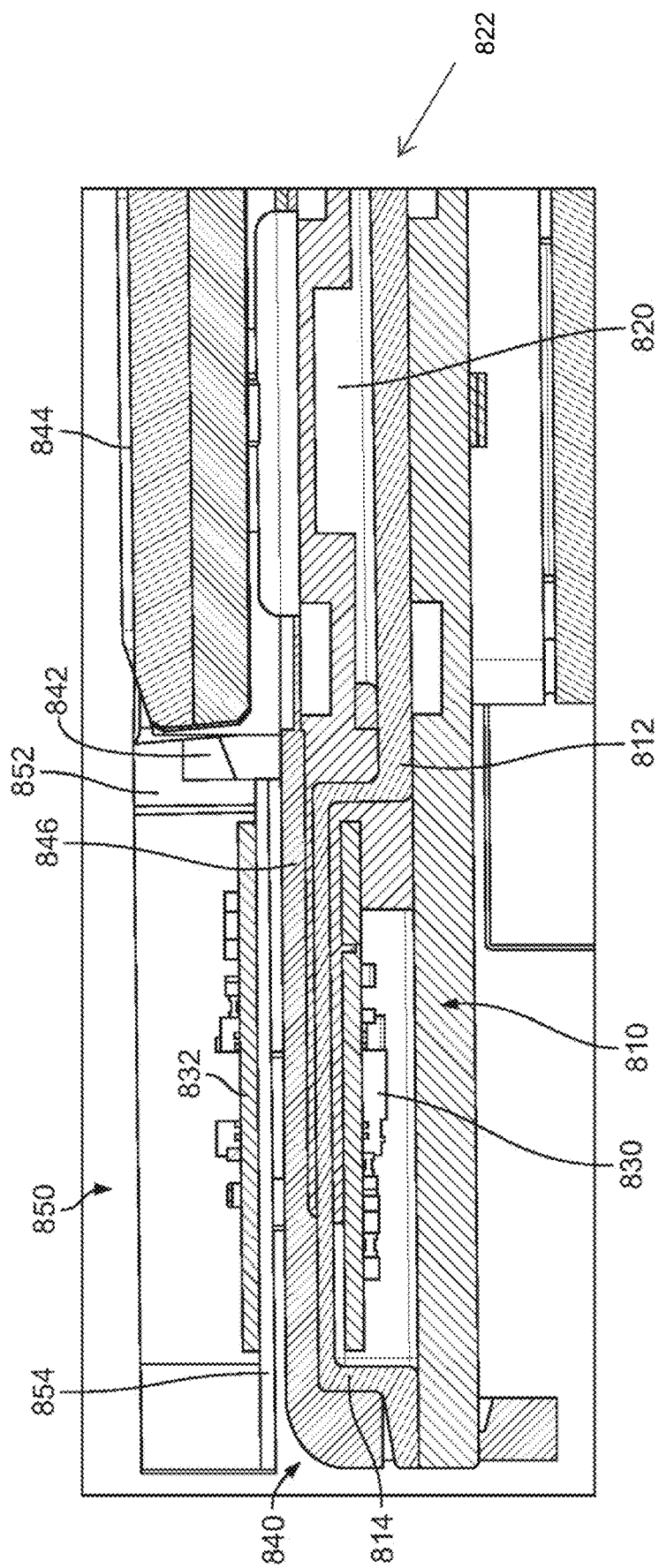
FIG. 8 is a detailed cross-sectional side view of a variation of a tool driver and surgical tool including respective electronic communication devices.

In some variations, a tool driver may comprise an electronic communication device configured to communicate wirelessly with a corresponding electronic communication device of a surgical tool. This may allow the system to perform a number of functions with the surgical tool. For example, the tool driver may communicate with the surgical tool to identify and authenticate the surgical tool, determine compatibility, download tool usage information (e.g., log data), configure settings of the surgical tool, communicate calibration data, or the like. FIG. 8 is a cross-sectional side view of a variation of a tool driver (810) coupled to a surgical tool (850) through a sterile adapter (840). As shown in FIG. 8, the tool driver (810) may comprise a first housing (812) configured to attach to a surgical tool (850) via a sterile adapter (840). The tool driver (810) may further comprise at least one output drive (822) coupled to a corresponding rotatable output drive disk (820) each supported by the first housing (812). The output drive (822) may be configured to communicate torque to an input drive (not shown) of the surgical tool (850) through the sterile adapter (840). The first housing (812) may comprise a first electronic communication device (830) disposed substantially in a plane of the output drive disk (820). The first electronic communication device (830) may be configured to wirelessly communicate with the surgical tool (850).

In some variations, a proximal end of the first housing (812) may be configured to support the first communication device (814) in a first communication portion (814). For example, the proximal end of the first housing (812) may comprise a projection (e.g., first communication portion (814)). The output drive disk (820) and first communication portion (814) may have substantially the same height.

In some variations, an electronic communication device may comprise a wireless communication board comprising radiofrequency (RF) circuitry (e.g., RF transceiver) including one or more of a receiver, transmitter, and/or optical (e.g., infrared) receiver and transmitter. RF circuitry may receive and transmit RF signals (e.g., electromagnetic signals) from the surgical tool and other devices. The RF circuitry converts between electrical signals and electromagnetic signals and communicates with other communications devices using the electromagnetic signals. The RF circuitry may include one or more of an antenna system, an RF transceiver, one or more amplifiers, a tuner, one or more oscillators, a digital signal processor, a CODEC chipset, a subscriber identity module (SIM) card, memory, and the like.

Short-range wireless communication using the electronic communication devices may use one or more communications standards, protocols and technologies including but not limited to Bluetooth, near-field communication (NFC), and radio-frequency identification (RFID). In some variations, the electronic communication device may be powered by a battery.

B. Sterile Adapter

In some variations, a sterile adapter may be configured to be interposed between a tool driver and surgical tool and formed in such a manner as to minimize a distance between their respective electronic communication devices. As shown in FIG. 8, the sterile adapter (840) may comprise a frame (842) configured to be interposed between the tool driver (810) and surgical tool (850). The frame (842) may be coupled to a plate assembly (not shown in FIG. 8). The frame (842) of the sterile adapter (840) may comprise a communication portion (846) configured to support a projection (854) of the surgical tool (850). The projection (854) may be substantially in a plane of the plate assembly when the surgical tool (850) is attached to the sterile adapter (840) and the plate assembly is biased toward the tool driver (810). Accordingly, when a second electronic communication device (832) is disposed in the projection (854), the second electronic communication device (832) may be substantially in a plane of the plate assembly. At least one rotatable coupler (844) may be supported by the plate assembly and configured to communicate torque from the output drive (822) of the tool driver (810) to the input drive of the surgical tool (850).

As shown in FIG. 8, a proximal end of the frame (842) may comprise the communication portion (846). In some variations, the communication portion (846) may attach to a proximal end of the first communication portion (814). The communication portion (846) may further support the projection (854) of the surgical tool housing (852). In some variations, the communication portion (846) of the frame (842) may be thinner than other portions of the frame (842) in order to reduce a distance between the communication devices (830, 832). In some variations, the frame (842) of the sterile adapter (840) may be formed without the communication portion (846) to allow the proximal ends of the tool driver (810) and surgical tool (850) to be brought closer together.

C. Surgical Tool

In some variations, a surgical tool may comprise an electronic communication device configured to communicate wirelessly with a corresponding electronic communication device of a tool driver. This may allow the surgical tool to perform a number of functions. For example, the surgical tool may communicate with the tool driver to identify and authenticate the tool driver and/or surgical system, determine compatibility, communicate calibration data, or the like. As shown in FIG. 8, the surgical tool (850) may comprise a second housing (852) configured to couple to the sterile adapter (840). The second housing (852) may comprise a projection. In some variations, an end effector (not shown) may extend from the second housing (852) and be operatively coupled to an input drive of the surgical tool (850). The input drive may be supported by the second housing (852) and be configured to receive torque communicated from the output drive (822) of the tool driver (810) through the sterile adapter (840). The second housing (852) may comprise a second communication device (832) configured to wirelessly communicate with the tool driver (810). The second communication device (832) may be disposed in the projection (854). The second communication device (832) may be of the same or different configuration as the first communication device (830) described herein.

In some variations, a proximal end of the surgical tool (850) may comprise the projection (854). For example, the projection (854) of the surgical tool (850) may be configured to support the second communication device (832). The output drive disk (830) and proximal end of the first housing (812) may have substantially the same height. One or more of the projection (854) and second communication device (832) may be disposed in substantially the same plane as the rotatable coupler (844). By providing the second electronic communication device (832) within the projection (854) that extends away from the surgical tool (850), the internal configuration of the surgical tool need not be modified to accommodate the electronic communication device. In some variations, the projection (854) having the second communication device (832) may be removably attached from the surgical tool (850). For example, a surface of the projection (854) facing the surgical tool (850) may comprise one or more fasteners (e.g., hooks) configured to couple to one or more of an underside of the surgical tool (850) and the frame (842) of the sterile adapter (840).

In some variations, when the surgical tool (850) and sterile adapter (840) are attached to the tool driver (810), a distance between the first and second communication devices (830, 832) may be less than about 10 mm. In some variations, the distance between the first and second communication devices (830, 832) may be less than about 6 mm. In some variations, the distance between the first and second communication devices (830, 832) may be between about 3 mm and about 6 mm. Generally, the plate assembly of the sterile adapter (840) may move relative to the frame (842) by more than about 5 mm. These short distances between the electronic communication devices may enable wireless power transfer to one or more devices of the surgical tool, such as the communication device and/or sensor. In some variations, the electronic devices may transfer power using one or more of inductive coupling and capacitive coupling.

III. Systems

Generally, the robotic surgical systems described herein may include a robotic arm and corresponding control system coupled to a tool driver, sterile adapter, and surgical tool. In some variations, a tool driver may comprise one or more sensors configured to generate sensor signals. Those signals may be received by a controller and used to generate attachment data corresponding to an attachment state between the tool driver, sterile adapter, and surgical tool. The control system may accordingly control one or more of the robotic arm and tool driver using the attachment data. As described in more detail herein, the controller may be coupled to one or more networks using a network interface. The controller may include a processor and memory coupled to a communication interface comprising a user interface. The controller may automatically perform one or more steps of a sterile barrier formation process, and thus improve a surgical tool switching process and reduce operator error by following a proper attachment sequence for engaging the sterile adapter and surgical tool to the tool driver.

Figure 9A:
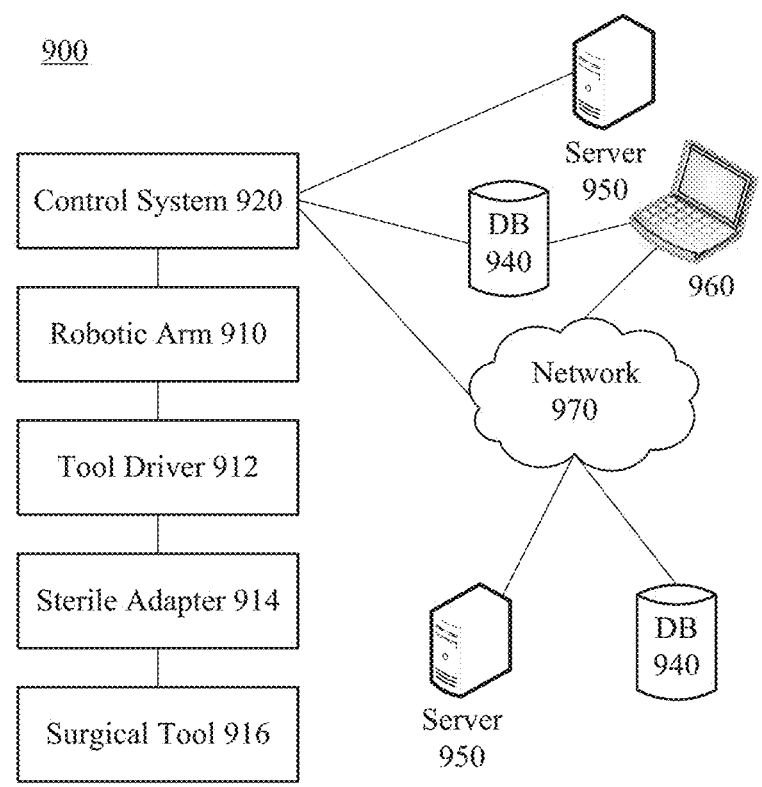
FIGS. 9A-9B are block diagram schematics of a variation of a robotic surgical system.
Figure 9B:
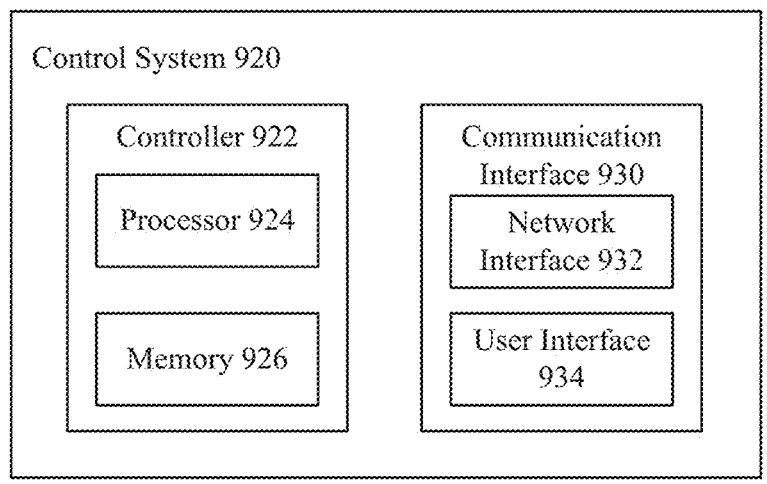

FIGS. 9A-9B are block diagrams of a variation of a robotic surgical system (900). The system (900) may comprise a control system (920) configured to control one or more of a robotic arm (910), tool driver (912), sterile adapter (914), and surgical tool (916). The robotic arms (910) may be located at a surgical platform (e.g., table, bed, etc.) having attached at a distal end one or more of a tool driver (912), sterile adapter (914), and surgical tool (916) (e.g., end effector). The robotic arm (910) may include a plurality of links that are actuated so as to position and orient the tool driver (912). The robotic arms (916) may be mounted on a table, in a cart, ceiling, sidewall, or other suitable support surface.

In some variations, the system (900) may include one or more sensors configured to generate sensor signals corresponding to an attachment state between two or more of the tool driver (912), sterile adapter (914), and surgical tool (916). For example, the sensors may be disposed in the tool driver and configured to sense one or more of a presence, engagement, and/or attachment of the tool driver to the sterile adapter and surgical tool. The tool driver (912), sterile adapter (914), and surgical tool (916) may be coupled to the control system (920) through one or more wired or wireless communication channels. Any wired connections may be optionally built into the floor and/or walls or ceiling. The control system (920) may be coupled to one or more networks (970), databases (940), and/or servers (950). The network (970) may comprise one or more databases (940) and servers (950). In some variations, a remote operator (not shown) may be coupled one or more networks (970), databases (940), and servers (950) through a user console (960) (e.g., surgeon bridge). In some variations, one or more of the tool driver (912) and surgical tool (916) may be coupled directly to any of the network (970), database (940), server (950), or each other. Processing, data generation, and analysis may be performed at any one of the devices of the system (900) or distributed throughout a plurality of devices.

A user (such as a surgeon or other operator) may use the user console (960) to remotely manipulate the robotic arms (910) and/or surgical tools (916) (e.g., tele-operation). The user console (960) may be located in the same procedure room as the robotic surgical system (900), in an adjacent or nearby room, or tele-operated from a remote location in a differently building, city, country, etc. In some variations, a plurality of user consoles (960) may be provided, for example to control additional surgical tools, and/or to take control of one or more surgical tools at a primary user console. The will permit, for example, a surgeon to take over or illustrate a technique during a surgical procedure with medical students and physicians-in-training, or to assist during complex surgeries requiring multiple surgeons acting simultaneously or in a coordinated manner.

Control System

The tool drivers, sterile adapters, and surgical tools as described herein may couple to one or more control systems (e.g., computer systems) and/or networks. FIG. 9B is a block diagram of the control system (920). The control system (920) may comprise a controller (922) comprising a processor (924) and a memory (926). In some variations, the control system (920) may further comprise one or more of a communication interface (930). The controller (922) may be coupled to the communication interface (930) to permit an operator to remotely control the control system (920), robotic arm (910), tool driver (912), surgical tool (916), sensors, and any other component of the system (900). The communication interface (930) may comprise a network interface (932) configured to connect the control system (920) to another system (e.g., Internet, remote server, database) over a wired and/or wireless network. The communication interface (930) may further comprise a user interface (934) configured to permit an operator to directly control the control system (920).

A. Controller

A control system (920), as depicted in FIG. 9B, may comprise a controller (922) in communication with the robotic surgical system (900) (e.g., robotic arm (910), tool driver (912), surgical tool (916)). The controller (920) may comprise one or more processors (924) and one or more machine-readable memories (926) in communication with the one or more processors (924). The processor (924) may incorporate data received from memory (926) and operator input to control the system (900). The memory (926) may further store instructions to cause the processor (924) to execute modules, processes and/or functions associated with the system (900). The controller (922) may be connected to one or more of the robotic arm (910), tool driver (912), and surgical tool (916) by wired and/or wireless communication channels. The controller (922) may be configured to control one or more components of the system (900), such as robotic arm (910), tool driver (912), surgical tool (916), communication interface (930), and the like.

The controller (922) may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on a surgeon bridge, servers or server computing devices such as routing/connectivity components, multiprocessor systems, microprocessor-based systems, distributed computing networks, personal computing devices, network appliances, portable (e.g., hand-held) or laptop devices. Examples of portable computing devices include smartphones, personal digital assistants (PDAs), cell phones, tablet PCs, wearable computers taking the form of smartwatches and the like, and portable or wearable augmented reality devices that interface with the operator's environment through sensors and may use head-mounted displays for visualization, eye gaze tracking, and user input.

i. Processor

The processor (924) may be any suitable processing device configured to run and/or execute a set of instructions or code and may include one or more data processors, image processors, graphics processing units, physics processing units, digital signal processors, and/or central processing units. The processor (924) may be, for example, a general purpose processor, Field Programmable Gate Array (FPGA), an Application Specific Integrated Circuit (ASIC), or the like. The processor (924) may be configured to run and/or execute application processes and/or other modules, processes and/or functions associated with the system and/or a network associated therewith. The underlying device technologies may be provided in a variety of component types including metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, combinations thereof, or the like.

ii. Memory

In some variations, the memory (926) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, combinations thereof, or the like. As used herein, database refers to a data storage resource. The memory (926) may store instructions to cause the processor (924) to execute modules, processes, and/or functions associated with the control system (920), such as sterile barrier formation, notification, robotic arm control, tool driver control, surgical tool control, sensor control, sensor signal processing, communication, authentication, or user settings, or the like. In some variations, storage may be network-based and accessible for one or more authorized users. Network-based storage may be referred to as remote data storage or cloud data storage. Sensor signal and attachment data stored in cloud data storage (e.g., database) may be accessible to respective users via a network, such as the Internet. In some variations, database (940) may be a cloud-based FPGA.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for a specific purpose or purposes.

Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs); holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and methods described herein may be performed by software (executed on hardware), hardware, or a combination thereof. Hardware modules may include, for example, a general-purpose processor (or microprocessor or microcontroller), a field programmable gate array (FPGA), an application specific integrated circuit (ASIC), or the like. Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

B. Communication Interface

The communication interface (930) may permit an operator to interact with and/or control the system (900) directly and/or remotely. For example, a user interface (934) of the system (900) may include an input device for an operator to input commands and an output device for an operator and/or other users (e.g., technicians) to receive output (e.g., view patient data on a display device) related to operation of the system (900). In some variations, a network interface (932) may permit the control system (920) to communicate with one or more of a network (970) (e.g., Internet), remote server (950), and database (940) as described in more detail herein.

i. User Interface

User interface (934) may serve as a communication interface between a user (e.g., operator) and the control system (920). In some variations, the user interface (934) may comprise an input device and output device (e.g., touch screen and display) and be configured to receive input data and output data from one or more sensors, input device, output device, network (970), database (940), and server (950). For example, sensor signals generated by a sterile adapter sensor and surgical tool sensor may be processed by processor (924) and memory (926), and output visually by one or more output devices (e.g., optical waveguides). Sensor signals and/or attachment data may be received by user interface (934) and output visually, audibly, and/or through haptic feedback through one or more output devices. As another example, operator control of an input device (e.g., joystick, keyboard, touch screen) may be received by user interface (934) and then processed by processor (924) and memory (926) for user interface (934) to output a control signal to one or more of the robotic arm (910), tool driver (912), and surgical tool (916). In some variations, the user interface (934) may function as both an input and output device (e.g., a handheld controller configured to generate a control signal while also providing haptic feedback to an operator).

In some variations, the devices, systems, and methods comprise one or more elements described in U.S. patent application Ser. No. 15/712,052, filed on Sep. 21, 2017, and titled "USER CONSOLE SYSTEM FOR ROBOTIC SURGERY," which is hereby incorporated by reference in its entirety.

1. Output Device

An output device of a user interface (934) may output sensor data corresponding to a patient and/or system (900), and may comprise one or more of an optical waveguide, display device, audio device, and haptic device. The display device may be configured to display a graphical user interface (GUI). The user console (960) may include an integrated display and/or video output that may be connected to output to one or more generic displays, including remote displays accessible via the internet or network. The video output or feed may also be encrypted to ensure privacy and all or portions of the video output may be saved to a server or electronic healthcare record system. A display device may permit an operator to view procedure data, attachment data, system data, tool data, patient data, and/or other data processed by the controller (922). In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

An audio device may audibly output patient data, tool data, attachment data, sensor data, system data, alarms and/or warnings. For example, the audio device may output an audible warning when improper attachment occurs between the tool driver, sterile adapter, and surgical tool. In some variations, an audio device may comprise at least one of a speaker, piezoelectric audio device, magnetostrictive speaker, and/or digital speaker. In some variations, an operator may communicate with other users using the audio device and a communication channel.

A haptic device may be incorporated into one or more of the input and output devices to provide additional sensory output (e.g., force feedback) to the operator. For example, a haptic device may generate a tactile response (e.g., vibration) to confirm operator input to an input device (e.g., joystick, keyboard, touch surface). In some variations, the haptic device may include a vibrational motor configured to provide haptic tactile feedback to a user. Haptic feedback may in some variations confirm attachment and detachment of the sterile adapter or surgical tool to the tool driver. Additionally or alternatively, haptic feedback may notify that operation of the tool driver is inhibited from driving an output drive due to improper attachment and/or detachment in order to prevent potential harm to the operator and/or system.

In some variations, the devices, systems, and methods comprise one or more elements described in U.S. Patent Application Ser. No. 62/432,538, filed on Dec. 9, 2016, and titled "USER INTERFACE DEVICES FOR USE IN ROBOTIC SURGERY," which is hereby incorporated by reference in its entirety.

2. Input Device

Some variations of an input device may comprise at least one switch configured to generate a control signal. In some variations, the input device may comprise a wired and/or wireless transmitter configured to transmit a control signal to a wired and/or wireless receiver of a controller (922). For example, an input device may comprise a touch surface for an operator to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, pointing device (e.g., mouse), trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio and recognize an operator voice as a control signal.

ii. Network Interface

As depicted in FIG. 9A, a control system (920) described herein may communicate with one or more networks (970) and computer systems (950) through a network interface (932). In some variations, the control system (920) may be in communication with other devices via one or more wired and/or wireless networks. The network interface (932) may facilitate communication with other devices over one or more external ports (e.g., Universal Serial Bus (USB), multi-pin connector) configured to couple directly to other devices or indirectly over a network (e.g., the Internet, wireless LAN).

In some variations, the network interface (932) may comprise a radiofrequency receiver, transmitter, and/or optical (e.g., infrared) receiver and transmitter configured to communicate with one or more devices and/or networks. The network interface (932) may communicate by wires and/or wirelessly with one or more of the sensors, user interface (934), network (970), database (940), and server (950).

In some variations, the network interface (930) may comprise radiofrequency (RF) circuitry (e.g., RF transceiver) including one or more of a receiver, transmitter, and/or optical (e.g., infrared) receiver and transmitter configured to communicate with one or more devices and/or networks. RF circuitry may receive and transmit RF signals (e.g., electromagnetic signals). The RF circuitry converts electrical signals to/from electromagnetic signals and communicates with communications networks and other communications devices via the electromagnetic signals. The RF circuitry may include one or more of an antenna system, an RF transceiver, one or more amplifiers, a tuner, one or more oscillators, a digital signal processor, a CODEC chipset, a subscriber identity module (SIM) card, memory, and the like. A wireless network may refer to any type of digital network that is not connected by cables of any kind.

Examples of wireless communication in a wireless network include, but are not limited to cellular, radio, satellite, and microwave communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, near-field communication (NFC), radio-frequency identification (RFID), Wireless Fidelity (Wi-Fi) (e.g., IEEE 802.11a, IEEE 802.11b, IEEE 802.11g, IEEE 802.11n), Voice over Internet Protocol (VoIP), Wi-MAX, a protocol for email (e.g., Internet Message Access Protocol (IMAP), Post Office Protocol (POP)), instant messaging (e.g., eXtensible Messaging and Presence Protocol (XMPP), Session Initiation Protocol for Instant Messaging, Presence Leveraging Extensions (SIMPLE), Instant Messaging and Presence Service (IMPS)), Short Message Service (SMS), or any other suitable communication protocol. Some wireless network deployments combine networks from multiple cellular networks or use a mix of cellular, Wi-Fi, and satellite communication.

In some variations, a wireless network may connect to a wired network in order to interface with the Internet, other carrier voice and data networks, business networks, and personal networks. A wired network is typically carried over copper twisted pair, coaxial cable, and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). As used herein, network refers to any combination of wireless, wired, public, and private data networks that are typically interconnected through the Internet, to provide a unified networking and information access system.

The foregoing description, for purposes of explanation, used specific nomenclature to provide a thorough understanding of the invention. However, it will be apparent to one skilled in the art that specific details are not required in order to practice the invention. Thus, the foregoing descriptions of specific variations of the invention are presented for purposes of illustration and description. They are not intended to be exhaustive or to limit the invention to the precise forms disclosed; obviously, many modifications and variations are possible in view of the above teachings. The variations were chosen and described in order to best explain the principles of the invention and its practical applications, and they thereby enable others skilled in the art to best utilize the invention and various implementations with various modifications as are suited to the particular use contemplated. It is intended that the following claims and their equivalents define the scope of the invention.

We claim:

1. A tool driver for use in a robotic surgical system, the tool driver comprising:

a housing configured to couple to a sterile adapter, the housing comprising a first side defining a distal end of the housing and having a sterile adapter engagement feature mateable with a corresponding tool driver engagement feature on the sterile adapter, and a sterile adapter sensor configured to generate a sensor signal when the tool driver engagement feature is mated with its corresponding sterile adapter engagement feature; and at least one rotatable output drive supported by a second side of the housing and configured to communicate torque to an input drive of a surgical tool through the sterile adapter, and wherein the second side is perpendicular to the first side such that the at least one rotatable output drive is arranged perpendicular to the first side having the tool driver engagement feature and the sterile adapter sensor.

2. The tool driver of claim 1, wherein the sterile adapter engagement feature comprises one or more of a recess and a projection.

3. The tool driver of claim 1, wherein the sterile adapter sensor is configured to generate the sensor signal when the tool driver engagement feature contacts the sterile adapter sensor.

4. A robotic surgical system comprising:
   a tool driver comprising:
   a first housing configured to attach to a surgical tool via a sterile adapter, the first housing comprising at least one projection extending from a surface of the first housing and configured to bias away from the surface, the projection comprising a surgical tool sensor configured to generate a sensor signal comprising at least one attachment state between the tool driver and the surgical tool, and the surgical tool sensor comprises a proximity sensor comprising a magnet coupled to a first end of the projection facing the surgical tool and a magnetic field transducer coupled to a second end of the projection; and
   at least one rotatable output drive supported by the first housing and configured to communicate torque to an input drive of the surgical tool through the sterile adapter.

5. The system of claim 4, wherein the projection is disposed between a pair of the rotatable output drives.

6. The system of claim 4, wherein the first housing comprises a plurality of the projections arranged in a bilaterally symmetrical arrangement.

7. The system of claim 4, wherein the projection comprises a compliant material.

8. The system of claim 4, wherein the projection comprises at least one of a coil spring and a leaf spring.

9. The system of claim 4, further comprising a second surgical tool sensor disposed at a distal end of the first housing.

10. The system of claim 9, wherein the second surgical tool sensor comprises a proximity sensor comprising a magnetic field transducer.

11. The system of claim 4, further comprising: a surgical tool comprising:
    a second housing configured to attach to the sterile adapter, the second housing comprising a sterile adapter engagement feature comprising a magnetic projection;
    at least one input drive supported by the second housing and configured to receive the torque communicated from an output drive of the tool driver through the sterile adapter; and
    an end effector extending from the second housing and operatively coupled to the input drive.

12. The system of claim 11, wherein the magnetic projection comprises a first tapered surface and a second tapered surface opposite the first tapered surface.

13. The system of claim 12, wherein a distal end of the surgical tool comprises the sterile adapter engagement feature.

14. The system of claim 4, wherein the surgical tool sensor generates a sensor signal corresponding to a plurality of attachment states between the tool driver and the surgical tool, and the plurality of attachment states comprise partial attachment, full attachment, partial detachment, full detachment, and improper attachment.

15. The system of claim 4, wherein the first housing comprises a plurality of the projections arranged in a bilaterally symmetrical arrangement.

* * * * *